US007164021B2

(12) United States Patent
Welsh et al.

(10) Patent No.: US 7,164,021 B2
(45) Date of Patent: Jan. 16, 2007

(54) OPIATE ANALOGS SELECTIVE FOR THE δ-OPIOID RECEPTOR

(75) Inventors: William J. Welsh, Princeton, NJ (US); Seong Jae Yu, Pennington, NJ (US); Anil Nair, Oro Valley, AZ (US)

(73) Assignee: The Curators of The University of Missouri, Columbia, MO (US)

( * ) Notice: Subject to any disclaimer, the term of this patent is extended or adjusted under 35 U.S.C. 154(b) by 279 days.

(21) Appl. No.: 10/665,377

(22) Filed: Sep. 18, 2003

(65) Prior Publication Data
US 2004/0122230 A1    Jun. 24, 2004

Related U.S. Application Data

(60) Provisional application No. 60/411,724, filed on Sep. 18, 2002.

(51) Int. Cl.
C07D 471/02    (2006.01)
C07D 471/08    (2006.01)
(52) U.S. Cl. .............................. 546/44; 546/45; 546/46
(58) Field of Classification Search ............... 514/280; 546/44, 45, 46
See application file for complete search history.

(56) References Cited

U.S. PATENT DOCUMENTS

| 4,816,586 | A | 3/1989 | Portoghese | 544/340 |
|---|---|---|---|---|
| 5,298,622 | A | 3/1994 | Portoghese et al. | 546/15 |
| 5,436,249 | A | 7/1995 | Dappen et al. | 514/279 |
| 5,457,208 | A | 10/1995 | Portoghese et al. | 546/35 |
| 5,578,725 | A | 11/1996 | Portoghese et al. | 546/35 |
| 5,852,030 | A | 12/1998 | Nagase et al. | 514/279 |
| 5,922,887 | A | 7/1999 | Dondio et al. | 548/539 |
| 6,177,438 | B1 * | 1/2001 | Nagase et al. | 514/280 |
| 6,359,111 | B1 | 3/2002 | Meyer et al. | 530/302 |

FOREIGN PATENT DOCUMENTS

| EP | 0663401 | * | 6/2000 |
|---|---|---|---|
| WO | WO 99/67206 | | 12/1999 |

OTHER PUBLICATIONS

Kotick, J Med Chem, vol. 24, pp. 1445-1450, 1981.*
Portoghese, J Med Chem, vol. 37, pp. 579-585, 1994.*
Anathan, J Med Chem, vol. 42, 3527-3538, 1999.*
Abdelhamid et al., "Selective blockage of Delta opiod receptors prevents the development of morphine tolerance and dependence in mice," *J. Pharmacol. Exp. Ther.*, 258(1):299-303, 1991.
Akil et al., "Endogenous opioids: biology and function," *Annual Rev. Neurosci.*, 7:223-255, 1984.
Ananthan et al., "Synthesis, opioid receptor binding, and bioassay of naltrindole analogues substituted in the indolic benzene moiety," *J. Med. Chem.*, 41(15):2872-2881, 1998.
Ananthan et al., "Synthesis, opioid receptor binding, and biological activities of naltrexone-derived pyrido- and pyrimidomorphinans," *J. Med. Chem.*, 42(18):3527-3538, 1999.

Bertolucci et al., "Microdialysis of opioid peptide release from the nucleus accumbens and ventrical pallidum of the freely moving rat," *Neurosci. Abstr.*, 18L1368, 1992.
Blisky et al., "SNC 80, a selective, nonpeptidic and systemically active opioid delta agonist," *J. Pharmacol. Exp. Ther.*, 273(1):359-366, 1995.
Bradbury et al., "Biosynthetic origin and receptor conformation of methionine enkephalin," *Nature*, 260:165-166, 1976.
Conn et al., "An unusual fischer indole synthesis with 4-keto acids: an indole incorporating the terminal hydrazine nitrogen," *J. Org. Chem.*, 55(90):2908-2913, 1990.
Coombs et al., "Intrathecal morphine tolerance: use of intrathecal clonidine, DADLE, and intraventricular morphine," *Anesthesiology*, 62(3):358-363, 1985.
Cramer III et al., "Comparative molecular field analysis (CoMFA). 1. Effect of shape on binding of steroids to carrier proteins," *J. of the Am. Chem. Soc.*, 110(18):5959-5967, 1988.
Dressman and Lennérnas, In: *Oral Drug Absorption: Prediction and Assessment (Drugs and the Pharmaceutical Sciences)*, vol. 106, 2000.
Foley, In: *Handbook of Experimental Pharmacology*, Herz (ed.), vol. 104/II: Opioids II, Springer-Verlag, Berlin, 693-743, 1993.
Gomes-Flores and Weber, "Differential effects of buprenorphine and morphine on immune and neuroendocrine functions following acute administration in the rat mesencephalon periaqueductal gray," *Immunopharm.*, 48:145-156, 2000.
Hardman and Limbird, In: *Goodman & Gilman's The Pharmacological Basis of Therapeutics*, 10th ed., McGraw-Hill Professional Publishing, 2001.
House et al., "Suppression of immune function by non-peptidic delta opioid receptor antagonists," *Neurosci. Lett.*, 198:119, 1995.
Hughes et al., "Identification of two related pentapeptides from the brain with potent opiate agonist activity," *Nature*, 258:577-579, 1975.
Kaliszan et al., "Gradient HPLC in the determination of drug lipophilicity and acidity," *Pure Appl. Chem.*, 73:1465-1475, 2001.
Knapp et al., "Properties of TAN-67, a nonpeptidic δ-opioid receptor agonist, at cloned human δ- and μ-opioid receptors," *Eur. J. Pharmacol.*, 291(2):129-134, 1995.
Knapp et al., "Structure-activity relationships for SNC80 and related compounds at cloned human delta and mu opioid receptors," *J. Pharmacol. Exp. Ther.*, 277(3):1284-1291, 1996.
Koob et al., "Neural substrates of opiate withdrawal," *TINS*, 15(5):186-191, 1992.

(Continued)

Primary Examiner—D. Margaret Seaman
(74) Attorney, Agent, or Firm—Fulbright & Jaworski LLP

(57) ABSTRACT

Novel compounds which selectively bind to the δ-opioid receptor have been designed. These compounds have greater selectivity, improved water (blood) solubility, and enhanced therapeutic value as analgesics. Because agonists with selectivity for the δ-opioid receptor have shown promise in providing enhanced analgesia without the addictive properties, the compounds of the present invention are better than morphine, naltrindole (NTI), spiroindanyloxymorphone (SIOM), and other known μ-opioid receptor selectors as analgesics.

9 Claims, 6 Drawing Sheets

OTHER PUBLICATIONS

Liao et al., "De novo design, synthesis, and biological activities of high-affinity and selective non-peptide agonists of the δ-opioid receptor," *J. Med. Chem.*, 41(24):4767-4776, 1998.

Loh et al., "Molecular characterization of opioid receptors," *Annu. Rev. Pharmacol. Toxicol.*, 30:123-147, 1990.

Lutz and Pfister, "Opioid receptors and their pharmacological profiles," *J. Receptor Res.*, 12(3):267-286, 1992.

Martin, "Pharmacology of opioids," *Pharmacol. Rev.*, 35(4):283-323, 1983.

Okawa et al., "7-arylindenenaltrexones as selective δ1 opioid receptor antagonists," *J. Med. Chem.*, 41:4177-4180, 1998.

Olson et al., "Endogenous opiates: 1988," *Peptides*, 10:1253-1280, 1989.

Pert and Snyder, "Opiate receptor: demonstration in nervous tissue," *Science*, 179(4077):1011-1014, 1973.

Pfeiffer et al., "Psychotomimesis mediated by $/kappa $ opiate receptors," *Science*, 233(4765):774-776, 1986.

Plobeck et al., "New diarylmethylpiperazines as potent and selective nonpeptidic δ opioid receptor agonists with increased in vitro metabolic stability," *J. Med. Chem.*, 43(21):3887-3894, 2000.

Olmsted et al., "A remarkable change of opioid receptor selectivity on the attachment of a peptidomimetic κ address element to the δ antagonist, natrindole: 5'[(N2-alkylamindino)methyl]naltrindole derivatives as a novel class of κ opioid receptor antagonists," *J. Med. Chem.*, 36:179-180, 1993.

Portoghese et al., "7-arylidenenaltrexones as selective δ1 opioid receptor antagonists," *J. Med. Chem.*, 41:4177-4180, 1998.

Raynor et al., "Pharmacological characterization of the cloned κ-, δ-, and μ- opioid receptors," *Molecular Pharmacol.*, 45:330-334, 1994.

Reid et al., "Naltrindole, and opioid delta receptor antagonist, blocks cocaine-induced facilitation of responding for rewarding brain stimulation," *Life Sci.*, 52:PL67-71, 1993.

Saltzman, In: *Drug Delivery: Engineering Principles for Drug Therapy (Topics in Chemical Engineering)*, Oxford University Press, 2001.

Schiller et al., "The opioid μ agonist/δ antagonist DIPP-NH2[Ψ] produces a potent analgesic effect, no physical dependence, and less tolerance than morphine in rats," *J. Med. Chem.*, 42(18):3520, 1999.

Sharp and Yaksh, "Pain killers of the immune system," *Nat. Med.*, 3(8):831-832, 1997.

Simon, "Opioid receptors and endogenous opioid peptides," *Medicinal Res. Rev.*, 11(4):357-374, 1991.

Stevens et al., "Potent and selective indolomorphinan antagonists of the kappa-opioid receptor," *J. Med. Chem.*, 43(14):2759-2769, 2000.

Takemori and Portoghese, "Selective natrexone-derived opioid receptor antagonists," *Annu. Rev. Pharmacol. Toxicol.*, 32:239-269, 1992.

Wei et al., "N,N-diethyl-4-(phenylpiperidin-4-ylidenemethyl)benzamide: a novel exceptionally selective, potent δ opioid receptor agonist with oral bioavailability and its analogues," *J. Med. Chem.*, 43(21):3895-905, 2000.

Peng et al., "3D-QSAR comparative molecular field analysis on opioid receptor antagonists: pooling data from different studies," *Journal of Medicinal Chemistry*, 48(5):1620-1629, 2005.

Peng et al., "3D-QSAR comparative molecular field analysis on opioid receptor agonists SNC80 and its analogs," *Journal of Molecular Graphics & Modeling*, submitted Jan. 31, 2005.

Gao et al., "Synthesis of 7-arylmorphinans. Probing the address requirements for selectivity at opioid delta receptors," *J Med Chem*, 41(16):3091-8, 1998.

\* cited by examiner

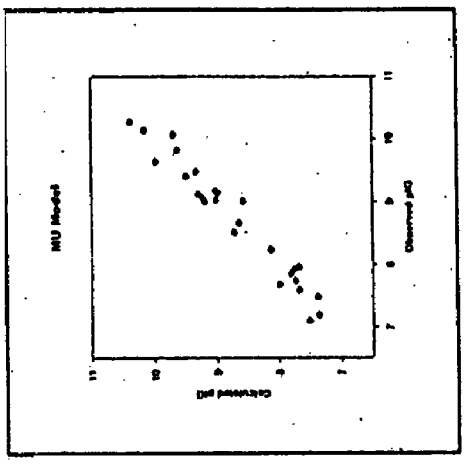
FIG. 2C (c) Mu
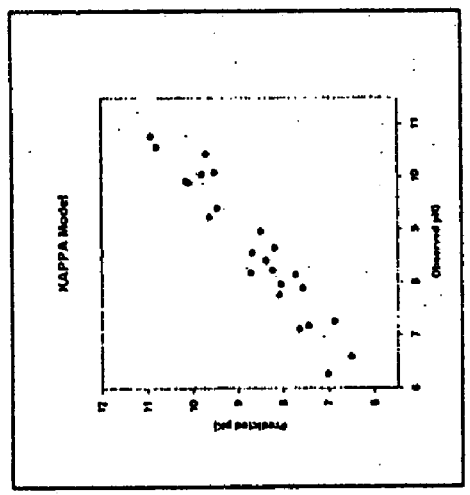
FIG. 2B (b) Kappa
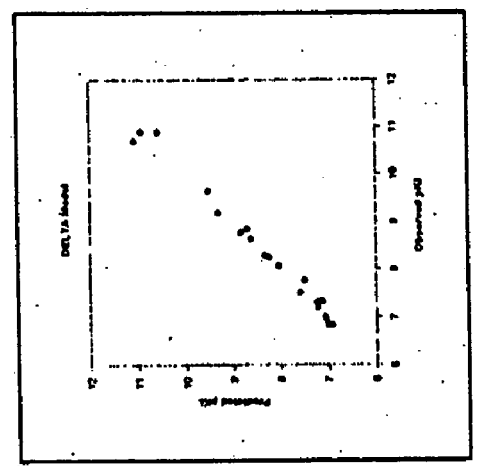
FIG. 2A (a) Delta

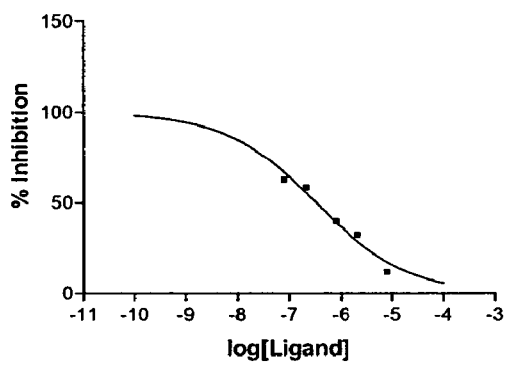 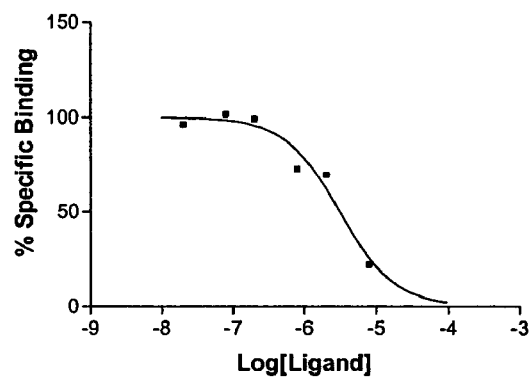
FIG. 7A                               FIG. 7B

OPIATE ANALOGS SELECTIVE FOR THE δ-OPIOID RECEPTOR

The present application claims priority to co-pending U.S. Provisional Application, Ser. No. 60/411,724 filed Sep. 18, 2002. The entire text of the above-referenced disclosure is specifically incorporated herein by reference without disclaimer.

BACKGROUND OF THE INVENTION

1. Field of the Invention

The present invention relates generally to the fields of pharmacology and more specifically to compounds and treatments for pain management, immune disorders, and drug addiction. More particularly, it provides a variety of compositions and methods based on novel opiate analogs having improved δ opioid receptor selectivity.

2. Description of Related Art

Opioid analgesics are well known for their ability to reduce the perception of pain without a loss of consciousness. Opium, the source of natural opiates, contains a variety of opiates including the familiar morphine and codeine. Morphine possesses a variety of effects, among which are increased tolerance to pain (analgesia), somnolence, euphoria, antitussive activity, respiratory depression, constipation and emesis. However, use of morphine is complicated by the highly addictive nature of this narcotic. The scientific community has focused a significant amount of time and effort to find opioid analogs that exhibit the analgesic activity of morphine and related opioids but possess improved oral bioavailability and a diminished risk associated with addiction and other undesirable side effects.

At least three major types of opioid receptors (δ, μ, κ) are involved in the modulation of a variety of opioid effects. In the field of opioid research, selective agonists for the δ-opioid receptor have shown promising therapeutic potential as analgesics without the adverse side effects associated with morphine and other opioid drugs which are selective for the μ-opioid receptor. The published literature contains numerous references to the design and synthesis of novel opioids, but only a few successful attempts have been reported in the development of non-peptide δ-opioid receptor agonists. Several examples of non-peptide ligands have been discovered either by modification of morphine-type alkaloids or by random screening approaches (Portoghese et al., 1993; Knapp et al., 1995; Knapp et al., 1996), but most of these suffer from various problems such as poor selectivity and low efficacy in vivo. Liao et al. (1998) recently reported the design, synthesis, and biological activity of non-peptide compounds that target the δ-opioid receptor. Portoghese et al. (1998) also described modifications of their "message" and "address" concept for designing receptor-specific opioid agonists and antagonists that confer selectivity for the δ-opioid receptor. Other reports of opioids selective for the δ receptor have also appeared (Ananthan et al., 1998; Ananthan et al., 1999; Schiller et al., 1999; Plobeck et al., 2000; Wei et al., 2000; WO 99/67203; WO 99/67206; U.S. Pat. No. 5,298,622; U.S. Pat. No. 4,816,586; U.S. Pat. No. 5,457,208; and U.S. Pat. No. 6,359,111).

However, there remains a need for non-peptide opioid compounds selective for the δ receptor with improved oral bioavailability and a diminished risk associated with addiction and other undesirable side effects.

SUMMARY OF THE INVENTION

Thus, in accordance with the present invention, there is provided a compound having the formula:

wherein

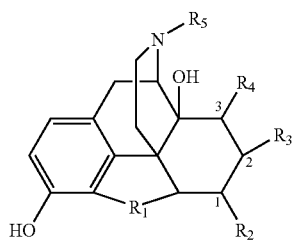

$R_1$ is O, NH, $NR_6$, S, SH, or $SR_6$; or more preferably O or NH;

$R_2$ is H, =O, t-butyl, phenoxy, diphenylamine, thiophenyl, phenyl, or cyclohexane; or more preferably H or =O;

$R_3$ is phenyl or phenoxy; or wherein $R_2$ and $R_3$ can optionally comprise a ring system selected from:

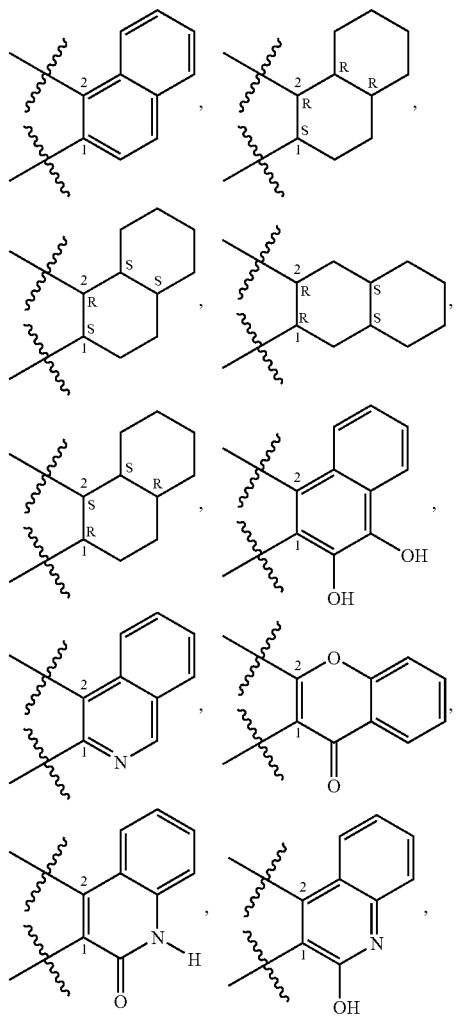

-continued

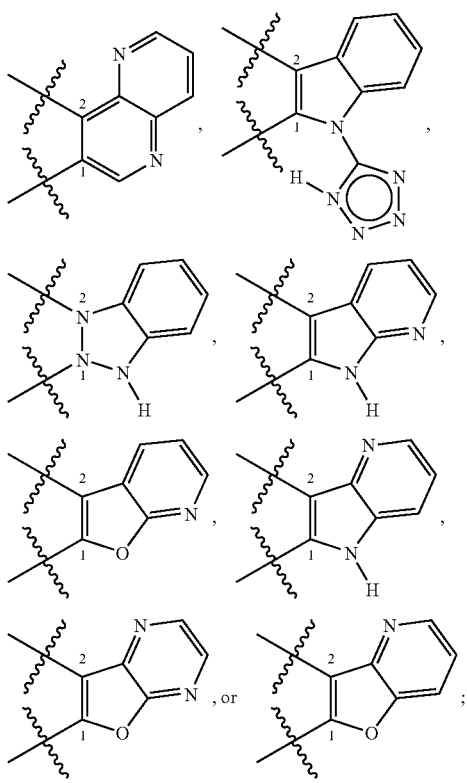

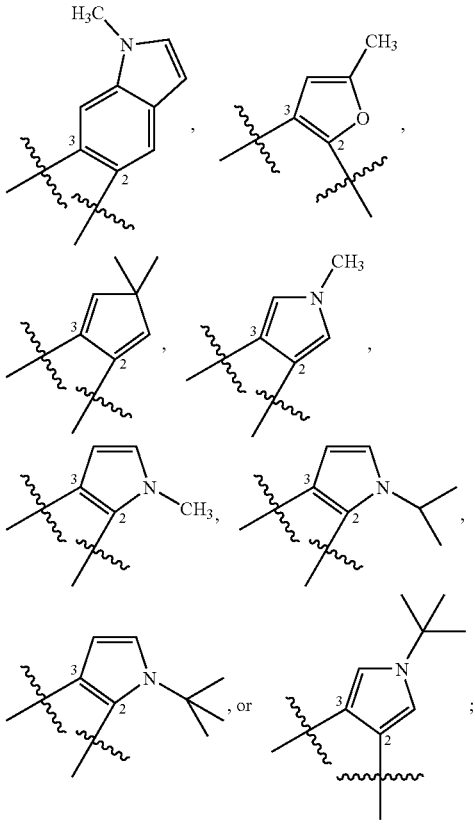

or wherein $R_3$ and $R_4$ can optionally comprise a ring system selected from:

or
$R_4$ is H or t-butyl; and
$R_5$ is $CH_3$, methylcyclopropane, a linear alkyl, a branched alkyl, a substituted alkyl, or a substituted branched alkyl; or
$R_6$ is H, $CH_3$, a linear alkyl, a branched alkyl, a substituted alkyl, or a substituted branched alkyl;

or a pharmaceutically acceptable salt thereof.

In particular embodiments, the invention encompasses a pharmaceutical composition containing the compound of the invention and a pharmaceutically acceptable carrier.

In a further embodiment, the invention encompasses a method for treating disease mediated by the δ-opioid receptor which comprises administering an effective amount of a compound of the formula:

wherein
$R_1$ is O, NH, $NR_6$, S, SH, or $SR_6$; $R_2$ is H, =O, t-butyl, phenoxy, diphenylamine, thiophenyl, phenyl, or cyclohexane; $R_3$ is phenyl or phenoxy;

or wherein R₂ and R₃ comprise a ring system selected from:
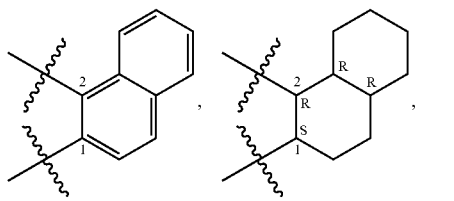
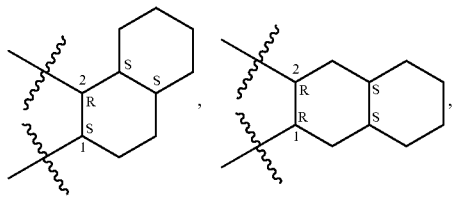
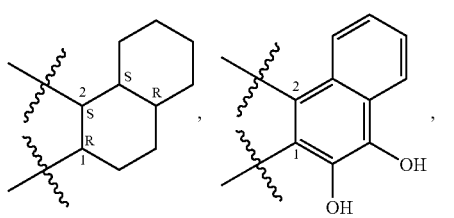
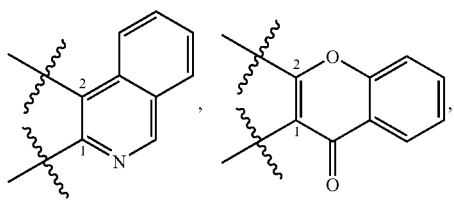
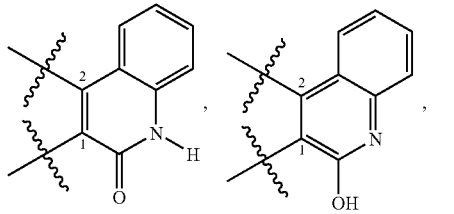
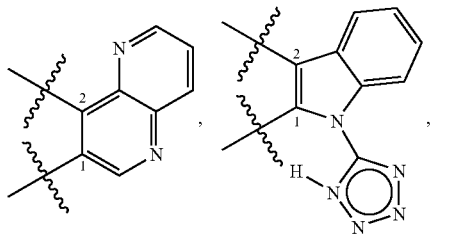
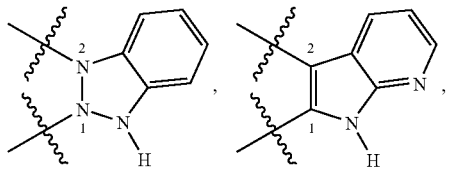
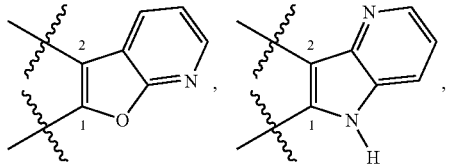
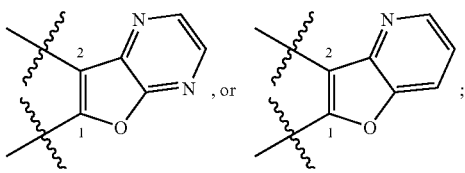
or wherein R₃ and R₄ comprise a ring system selected from:
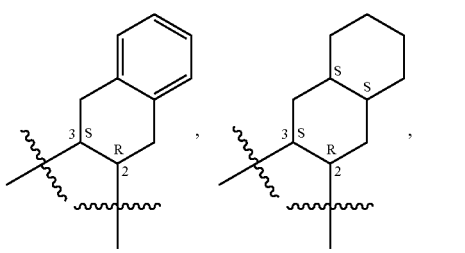
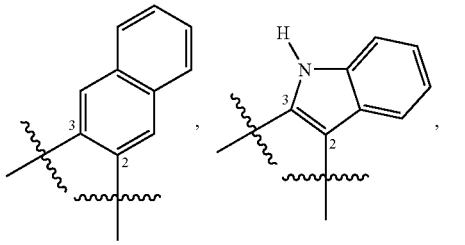
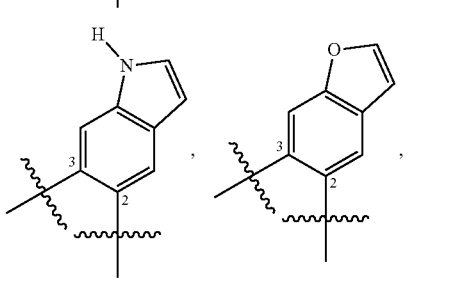
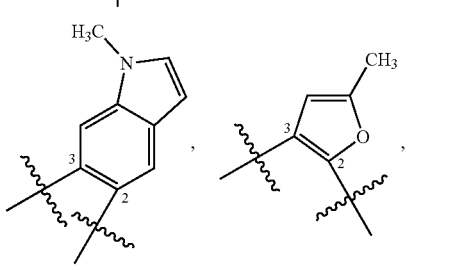
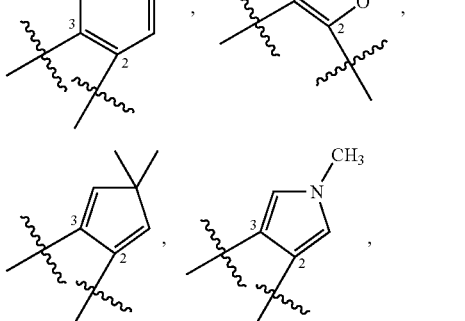
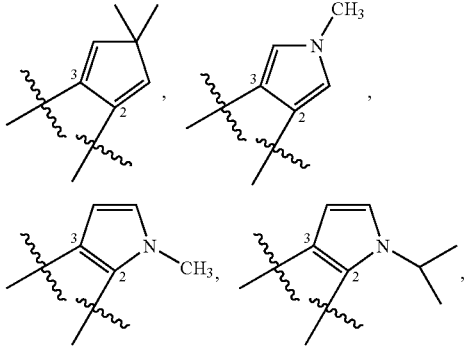

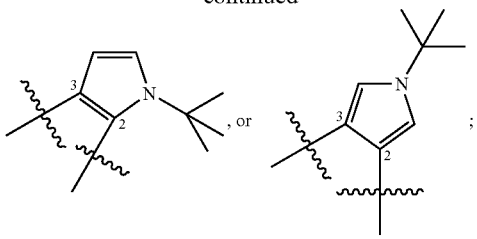

or $R_4$ is H or t-butyl; and $R_5$ is $CH_3$, methylcyclopropane, a linear alkyl, a branched alkyl, a substituted alkyl, or a substituted branched alkyl; or a pharmaceutically acceptable salt thereof.

Also provided is a method for treating a patient comprising administering a therapeutically effective amount of a compound of the present invention. A method for treating disease mediated by the δ-opioid receptor comprising administering an effective amount of a compound of the present invention is also provided. The disease may comprise of an immune disorder, transplant rejection, allergy, inflammation, drug or alcohol abuse, diarrhea, cardiovascular disease, or respiratory disease.

In yet another embodiment of the invention, methods are provided for treatment of a disease comprising treating pain, protecting brain cells, or decreasing gastric secretion.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A–2C. Plots of the CoMFA-predicted vs. experimentally observed binding affinities (pKi) for a series of known opioids (FIG. 2A) δ receptor data; (FIG. 2B) κ receptor data; (FIG. 2C) μ receptor data.

FIGS. 7A–7B. Competitive analysis of the opoid analogue DST3-2. FIG. 7A—Shows high delta binding affinity (140 nM) of the DST3-2 analogue. The percent inhibition of DST3-2 versus the delta receptor is shown using 1.64 nM of the reference compound [3]H-Bremazocine. FIG. 7B—Shows good delta/mu selectivity (~10/1) of the DST3-2 analogue. The percent specificity of DST3-2 versus the mu receptor is shown using 1.64 nM of the reference compound [3]H-Bremazocine.

DESCRIPTION OF ILLUSTRATIVE EMBODIMENTS

I. The Present Invention

Figure 1:
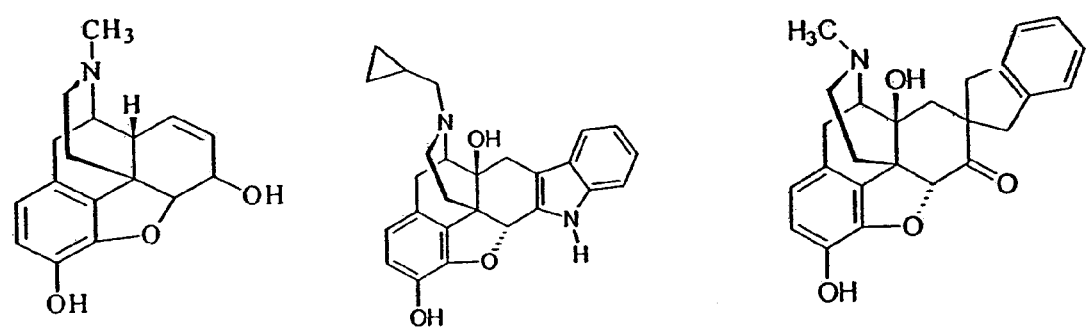
FIG. 1. Molecular structures of three opioids.

The use of opiate analogues for treating pain, immune disorders, or drug addiction can suffer from the problems of poor selectivity, low efficacy in vivo, poor oral bioavailability, risks associated with addiction and other undesirable side effects. There is great interest in the medical and pharmacological community in the development of δ-selective opioids, such as naltrindole (NTI) and spiroindanyloxymorphone (SIOM), that exhibit the analgesic activity of morphine and related opioids while possessing improved oral bioavailability and a diminished risked associated with addiction and other undesirable side effects thus showing promising therapeutic potential. The current methods used to discover opiate analogues rely on the modification of the morphine-type alkaloid structure or the random screening of structures for activity. However, these approaches also suffer from various drawbacks such as poor selectivity and low efficacy in vivo.

Thus, the present invention provides novel methods towards screening for δ-selective opioids. In addition synthetic routes for these novel δ-selective opioids are provided along with methods for the use of the novel δ-selective opioids. By virtue of their non-peptide chemical structure, these novel δ-selective opioids should exhibit superior oral tolerability and greater amenability to large-scale production over peptide based opioids such as the enkephalins.

II. Opioid Receptors

Opioid drugs have various effects on perception of pain, consciousness, motor control, mood, and autonomic function and can also induce physical dependence (Koob et al., 1992). The endogenous opioid system plays an important role in modulating endocrine, cardiovascular, respiratory, gastrointestinal and immune functions (Olson et al., 1989). Opioids exert their actions by binding to specific membrane-associated receptors located throughout the central and peripheral nervous system (Pert and Snyder, 1973). The endogenous ligands of these opioid receptors have been identified as a family of more than 20 opioid peptides that derive from the three precursor proteins proopiomelanocortin, proenkephalin, and prodynorphin (Hughes et al., 1975; Akil, et al., 1984). Although the opioid peptides belong to a class of molecules distinct from the opioid alkaloids, they share the common structural features of a positive charge juxtaposed with an aromatic ring which are required for interaction with the receptor (Bradbury et al., 1976).

Results from pharmacological studies suggest that there are numerous classes of opioid receptors, including those designated δ, κ, and μ (Simon, 1991; Lutz and Pfister, 1992). Biochemical characterization of opioid receptors from many groups report a molecular mass of about 60,000 Da for all three subtypes, suggesting that they could be related molecules (Loh et al., 1990). However, the three classes differ in their affinity for various opioid ligands and in their cellular distribution, and thus the three different classes of opioid receptors are believed to serve different physiological functions (Olson et al., 1989; Simon, 1991; Lutz and Pfister, 1992).

Among the three classes of opioid receptors, recent evidence suggests that δ-selective opioids could be potentially useful as analgesics devoid of the numerous undesirable side effects (e.g., respiratory depression, physical dependence and gastrointestinal effects) associated with narcotics such as morphine (Blisky et al., 1995). It is known that morphine interacts principally with the μ receptors, and peripheral administration of this opioid induces release of enkephalins (Bertolucci et al., 1992). The δ receptors bind with the greatest affinity to enkephalins and have a more discrete distribution in the brain than either μ or κ receptors, with high concentrations in the basal ganglia and limbic regions. Thus, enkephalins may mediate part of the physiological response to morphine, presumably by interacting with δ receptors.

Moreover, selective antagonists of δ receptors have been shown to modulate the development of tolerance and dependence to μ agonists such as morphine (Abdelhamid et al., 1991), to modulate the behavioral effects of drugs of abuse such as cocaine (Reid et al., 1993), and to elicit favorable immunomodulatory effects (House et al., 1995). The δ-selective opioid analogues thus represent extremely attractive candidates for a broad range of novel pharmaceutical applications including effective yet safe analgesics, immunomodulatory agents for treating immune disorders, and new treatments for drug addiction.

III. Opioids

The term opioid refers to all compounds in a generic sense related to opium. The word opium is derived from opos, the Greek word for juice, since the medicine was derived from the juice of the opium poppy, *papaver somniferum*. Opiates are drugs derived from opium, and include the natural products morphine, codeine, thebaine, and many semisynthetic congeners derived from them. Endogenous opioid peptides (EOPs) are the naturally synthesized ligands for opioid receptors. The term endorphin is used synonymously with EOP, but also refers to a specific endogenous opioid, β-endorphin. The term narcotic was derived from the Greek word for stupor. At one time, it referred to any drug that induced sleep, but then became particularly associated with opioids.

Opioids such as heroin and morphine exert their effects by mimicking naturally-occurring substances, termed the endogenous opioid peptides or endorphins. The endogenous opioid system has been found to have both molecular and biochemical complexity, as well as, widespread anatomy, and diversity. These diverse functions subsume a 'housekeeping role' in the body. They include the best-known sensory role, prominent in inhibiting responses to painful stimuli, a modulatory role in gastrointestinal, endocrine and autonomic functions; an emotional role, evident in the powerful rewarding and addicting properties of opioids; and a cognitive role in the modulation of learning and memory. Results from scientific studies have revealed the opioid system to be a complex and subtle system, with a great diversity in endogenous ligands (over a dozen), yet with only four major receptor types.

Of the four major receptor types, only three μ, δ, and κ have been extensively studied. The more recently discovered nociceptin/orphanin FQ receptor (N/OFQ receptor; also initially described as the opioid receptor-like 1 (ORL-1) or "orphan" opioid receptor) has added a new dimension to the study of opioids. Recently, a new nomenclature system has been proposed to reflect the consideration of this receptor as part of the opioid receptor family. It has been suggested by the IUPHAR Nomenclature Committee that these receptors be referred to as the OP (opioid peptide) receptor family and individual receptors be called the μ or MOP, δ or DOP, κ or KOP, and N/OFQ or NOP receptors.

A. Effects of Clinically Used Opioids

Morphine and most other clinically used opioid agonists exert their effects through μ receptors. These drugs affect a wide range of physiological systems, including, analgesia, mood, rewarding behavior, respiratory, cardiovascular, gastrointestinal, and neuroendocrine function. Delta opioid compounds are also potent analgesics in animals and humans (Coombs et al., 1985). Many δ agonists currently in use are peptidergic and unable to cross the blood-brain barrier, thus requiring intraspinal administration. The κ selective agonists produce analgesia that has been shown in animals to be mediated primarily at spinal sites. Respiratory depression and miosis may be less severe with κ than with μ agonists. Instead of euphoria, μ agonists produce dysphoric and psychotomimetic effects (Pfeiffer et al., 1986). In neural circuitry mediating both reward and analgesia, μ and κ agonists have been shown to have antagonistic effects. Mixed agonist-antagonist compounds were developed for clinical use with the hope that they would have less addictive potential and less respiratory depression. In practice, it has turned out that for the same degree of analgesia, the same intensity of side effects will be observed (APS 1999). A "ceiling effect," limiting the amount of analgesia attainable, is often seen with these compounds. Some drugs of this class, such as pentazocine and nalorphine, can produce severe psychotomimetic effects that are not naloxone reversible (which suggest that they are not mediated through classical opioid receptors). Also, these drugs can precipitate withdrawal in opioid tolerant patients. For these reasons, the clinical use of these compounds is relatively limited.

In human beings, morphine-like drugs produce analgesia, drowsiness, changes in mood, and mental clouding. A significant feature of the analgesia is that it occurs without loss of consciousness. When therapeutic doses of morphine are given to patients with pain, they report that the pain is less intense, less discomforting, or entirely gone; drowsiness commonly occurs. In addition to relief of distress, some patients experience euphoria.

When morphine in the same dose is given to a normal, pain-free individual, the experience may be unpleasant. Nausea is common, and vomiting also may occur. There may be feelings of drowsiness, difficulty in mentation, apathy, and lessened physical activity. As the dose is increased, the subjective, analgesic, and toxic effects, including respiratory depression, become more pronounced. Morphine does not have anticonvulsant activity and usually does not cause slurred speech, emotional lability, or significant motor incoordination. The relief of pain by morphine-like opioids is relatively selective, in that other sensory modalities are not affected. Patients frequently report that the pain is still present, but that they feel more comfortable. Continuous dull pain is relieved more effectively than sharp intermittent pain, but with sufficient amounts of opioid it is possible to relieve even the severe pain associated with renal or biliary colic.

While opioids are primarily used clinically for their pain modulatory properties, they produce a host of other effects. This is not surprising in view of the wide distribution of opioids and their receptors, both in the brain and in the periphery. Opioids can produce muscular rigidity in human beings; alter the equilibrium point of the hypothalamic heat-regulatory mechanisms; inhibit the release of gonadotropin-releasing hormone (GnRH) and corticotropin-releasing factor (CRF) in the hypothalamus; cause constriction of the pupil by an excitatory action on the parasympathetic nerve innervating the pupil; produce convulsions in animals; depress respiration, at least in part by virtue of a direct effect on the brainstem respiratory centers; depress the cough reflex, at least in part by a direct effect on a cough center in the medulla; cause nausea and vomiting by direct stimulation of the chemoreceptor trigger zone for emesis, in the area postrema of the medulla; cause orthostatic hypotension and fainting upon rising from a supine position; decrease the secretion of hydrochloric acid in the gastrointestinal tract; diminishes biliary, pancreatic, and intestinal secretions in the small intestine; diminishes or abolishes propulsive peristaltic waves in the colon; inhibit gastrointestinal propulsive activity in the bowels; increase the pressure in the common bile duct; increase the tone and amplitude of contractions of the ureter; and cause dilatation of cutaneous blood vessels in the skin. Opioids have been shown to modulate immune function both via direct, receptor-mediated effects on immune cells and indirectly via centrally mediated neuronal mechanisms (Gomez-Flores and Weber, 2000; Sharp and Yaksh, 1997). The overall effects of opioids on immune function appear to be suppressive, with increased susceptibility to infection and tumor spread observed in experimental studies.

B. Morphine and Related Opioids

Because the laboratory synthesis of morphine is difficult, the drug is still obtained from opium or extracted from poppy straw. Opium is obtained from the unripe seed capsules of the poppy plant, *Papaver somniferum*. The milky juice is dried and powdered to make powdered opium, which contains a number of alkaloids. Only a few—morphine, codeine, and papaverine—have clinical usefulness. These alkaloids can be divided into two distinct chemical classes, phenanthrenes and benzylisoquinolines. The principal phenanthrenes are morphine (10% of opium), codeine (0.5%), and thebaine (0.2%). The principal benzylisoquinolines are papaverine (1.0%), which is a smooth muscle relaxant, and noscapine (6.0%).

Many semisynthetic derivatives are made by relatively simple modifications of morphine or thebaine. Codeine is methylmorphine, the methyl substitution being on the phenolic hydroxyl group. Thebaine differs from morphine only in that both hydroxyl groups are methylated and that the ring has two double bonds. Thebaine has little analgesic action, but is a precursor of several important 14-OH compounds, such as oxycodone and naloxone. Certain derivatives of thebaine are more than 1000 times as potent as morphine (e.g., etorphine). Diacetylmorphine, or heroin, is made from morphine by acetylation at the 3 and 6 positions. Apomorphine, which also can be prepared from morphine, is a potent emetic and dopaminergic agonist. Hydromorphone, oxymorphone, hydrocodone, and oxycodone also are made by modifying the morphine molecule.

In addition to morphine, codeine, and the semisynthetic derivatives of the natural opium alkaloids, a number of other structurally distinct chemical classes of drugs have pharmacological actions similar to those of morphine. Clinically useful compounds include the morphinans, benzomorphans, methadones, phenylpiperidines, and propionanilides. Although the two-dimensional representations of these chemically diverse compounds appear to be quite different, molecular models show certain common characteristics; these are indicated by the heavy lines in the structure of morphine shown above. Among the important properties of the opioids that can be altered by structural modification are their affinity for various species of opioid receptors, their activity as agonists versus antagonists, their lipid solubility, and their resistance to metabolic breakdown. For example, blockade of the phenolic hydroxyl at position 3, as in codeine and heroin, drastically reduces binding to $\mu$ receptors; these compounds are converted to the potent analgesics morphine and 6-acetyl morphine, respectively, in vivo.

C. Side Effects of Opioids

Unfortunately, use of opioids can cause severe adverse side effects including somnolence, euphoria, antitussive activity, respiratory depression, emesis, changes in thermoregulation, inhibition of gastrointestinal motility, muscle rigidity, renal function, appetite, gastric secretion, learning and memory, mental illness, epileptic seizures and other neurological disorders, and the potential for physical dependence and abuse. The search for compounds exhibiting minimal adverse side effects has led to the synthesis and study of many opioid-like compounds.

The $\delta$ receptors, along with the related $\kappa$ and $\mu$ receptors, found on cells located throughout the central and peripheral nervous system normally bind with opioid peptides (e.g., enkephalins) that the body produces. By binding to the receptors, these peptides modulate endocrine, cardiovascular respiratory, gastrointestinal, and immune functions. Opioid narcotics are alkaloids, with molecular structures quite distinct from opioid peptides. However, the narcotic drugs and opioid peptides share common structural features (known as pharmacophores) that enable the drugs to bind to the opioid receptors. When they bind to these receptors, the narcotics exert various effects on the perception of pain, consciousness, motor control, mood, and autonomic function. They also induce physical dependence. However, recently published studies (Schiller et al., 1999) demonstrate that compounds (or combinations of compounds) that act in concert as $\mu$ agonists and $\delta$ antagonists exhibit the potency of opioids as pain killers yet without their negative side effects such as physical addiction. This study, among others, reveals that $\mu$ agonists/$\delta$ antagonists are very attractive targets as therapeutic agents. Similarly, opioid analogues specific for the $\delta$ receptor will potentially have much fewer or less severe side effects than analogues targeted at other opioid receptor types (Blisky et al., 1995).

The development of tolerance and physical dependence with repeated use is another characteristic feature of all the opioid drugs that may be lessened by using opioids having superior $\delta$ opioid receptor selectivity. Tolerance to the effect of opioids or other drugs simply means that over time, the drug loses its effectiveness at a specific dose level and an increased dose is required to produce the same physiological response. Dependence refers to a complex and poorly understood set of changes in the homeostasis of an organism that is caused by a disturbance of the homeostatic set point of the organism due to drug use cessation. This disturbance is often called withdrawal. Addiction is a behavioral pattern characterized by compulsive use of a drug and overwhelming involvement with its procurement and use. Tolerance and dependence are physiological responses seen in all patients and are not predictors of addiction. Cancer pain often requires prolonged treatment with high doses of opioids, leading to tolerance and dependence, but abuse in this setting is very unusual (Foley, 1993). Opioids can be discontinued in dependent patients once the need for analgesics is gone without subjecting them to withdrawal. Clinically, the dose can be decreased by 10–20% every other day and eventually stopped without signs and symptoms of withdrawal.

It has been suggested that highly selective opioid agonists or antagonists might have therapeutic applications, and that the potential side effects of such analogues mediated through other opioid receptors types can be minimized or eliminated. (Martin, 1983). Among the three classes of opioid receptors recent evidence suggests that $\delta$-selective opioids could be potentially useful as analgesics devoid of the numerous side effects (e.g., respiratory depression, physical dependence and gastrointestinal effects) associated with narcotics such as morphine (Blisky et al., 1995). Moreover, selective antagonists of δ receptors have been shown to modulate the development of tolerance and dependence to μ agonists such as morphine (Abdelhamid et al., 1991), to modulate the behavioral effects of drugs of abuse such as cocaine (Reid et al., 1993), and to elicit favorable immunomodulatory effects (House et al., 1995). The δ-selective opioids thus represent extremely attractive candidates for a broad range of novel pharmaceutical applications including powerful yet safe analgesics, immunomodulatory agents for treating immune disorders, and new treatments for drug addiction. The present invention provides novel opioid analogues and methods for predicting and producing these novel opioid analogues that target the δ opioid receptor.

IV. Non-Peptide Opioid Analogues

The basic design strategy for non-peptide opioid analogues is based on the "message-address" concept developed to rationalize the separate pharmacophoric features of opioids that confer affinity versus selectivity (Takemori and Portoghese, 1992). The "message" represents those structural features common to all opioids that are recognized similarly by the three types of receptors (δ, κ, μ). The "address" represents those specific structural features that confer high selectivity for a particular (e.g., δ) opioid receptor.

V. Uses for Non-Peptide Opioid (NPO) Analogues

The Non-Peptide Opioids (NPOs) of the current invention may be used for analgesis as well as a variety of other therapies. When used as an analgesic, the condition may be chronic pain, acute pain, pain caused by cancer, arthritis, migraines, etc. Other therapies that may be treated with the NOPs described herein include immunomodulators for autoimmune diseases such as arthritis, skin grafts, organ transplants, collagen diseases, allergies, anti-tumor agents, anti-viral agents, and surgical needs. The treatment of conditions such as diarrhea, depression, urinary inconsistency, mental illness, cough, lung edema, gastro-intestinal disorders and spinal injury is also considered. The NPOs may be used for the treatment of drug addiction, where the drug is an opioid or another substance such as alcohol or nicotine. "Disease" or "condition" for which compounds of the present invention are applicable include, but are not limited to, for example, the treatment of inflammation in a subject, and for treatment of other inflammation-associated disorders, such as, an analgesic in the treatment of pain and headaches, or as an antipyretic for the treatment of fever. Compounds of the invention may be useful to treat arthritis, including but not limited to rheumatoid arthritis, spondyloarthopathies, gouty arthritis, osteoarthritis, systemic lupus erythematosus, and juvenile arthritis. Compounds of the invention may be useful in the treatment of asthma, bronchitis, menstrual cramps, tendinitis, bursitis, and skin related conditions such as psoriasis, eczema, burns and dermatitis. Compounds of the invention also may be useful to treat gastrointestinal conditions such as inflammatory bowel disease, Crohn's disease, gastritis, irritable bowel syndrome, and ulcerative colitis, and for the prevention or treatment of cancer, such as colorectal cancer. Compounds of the invention may be useful in treating inflammation in such diseases as vascular diseases, migraine headaches, periarteritis nodosa, thyroiditis, aplastic anemia, Hodgkins disease, sclerodoma, rheumatic fever, type I diabetes, myasthenia gravis, multiple sclerosis, sarcoidosis, nephrotic syndrome, Behcet's syndrome, polymyositis, gingivitis, hypersensitivity, swelling occurring after injury, myocardial ischemia, and related diseases. The compounds may also be useful in the treatment of ophthalmic diseases, such as retinitis, retinopathies, conjunctivitis, uveitis, ocular photophobia, and of acute injury to the eye tissue. The compounds may also be useful in the treatment of pulmonary inflammation, such as that associated with viral infections and cystic fibrosis. The compounds may also be useful for the treatment of certain central nervous system disorders such as cortical dementias including Alzheimer's disease. The compounds of the invention may be useful as anti-inflammatory agents, such as for the treatment of arthritis, with the additional benefit of having significantly less harmful side effects, allergic rhinitis, respiratory distress syndrome, endotoxin shock and trauma. Compounds of the invention may be useful in interdicting or modifying the effects of other biologically active compounds such as narcotic addiction. Compounds of the invention may be useful for treating diseases or conditions other than ones associated with receptors, for example, blocking, inhibiting, or promoting, metabolic pathways or enzyme function, and selectively interacting with genetic material.

VI. Bioavailability of Opioid Analogues

The bioavailability and activity of the NPO's of the current invention for the δ receptor can be screened before use to determine their effectiveness. For example, a radioligand binding assay may be used to measure the bioavailability or activity of the NPOs of the current invention (U.S. Pat. No. 5,922,887). Bioavailability, which includes the absorption, distribution, metabolism, excretion (ADME) and toxicity of a compound, is often difficult to predict based on theoretical-computational methods. For true drug candidates, experimental tests are performed in vivo on animal models and the results are extrapolated to humans. Methods for determining bioavailibility can be found in a number of reference books covering the topic (Dressman, 2000; Hardman, 2001; or Saltzman, 2001). For screening purposes, one of ordinary skill can use log P to estimate the hydrophobic-hydrophilic balance and water solubility of a compound. The lopP value is determined experimentally or estimated computationally, where "P" refers to the "partitioning" of a compound between an organic phase (usually n-octanol) and an aqueous phase (water). HPLC and other modern experimental techniques can be used to determine bioavailability (Kaliszan, et al. 2001). Another technique used to determine bioavailibility is the traditional "shaker" procedure in which a compound is introduced into a separatory funnel containing equal amounts of n-octanol and water. After shaking the flask, containing the compound of the current invention, to achieve equilibrium, the amounts (concentrations) of compound in the organic phase and aqueous phase are measured. Log P is then calculated as the logarithm (base 10) of the ratio of the amount (or concentration) of compound in the organic phase relative to that in the aqueous phase (log P=log[organic]/[water]). Values schemes have been developed to estimate Log P values computationally. A more common value scheme method, such as C log P, estimates the Log P value of a compound by adding "C log P contributions" (stored in a database) from various fragments or components of the compound. Other "adjustment" terms can be added to correct for various inaccuracies using the C log P method (see on the World Wide Web BioByte website).

VII. Chemistry

A. Key Structural Groups

The "message-address" concept referred to above is illustrated in Table 1 using the δ-selective antagonist NTI and the δ-selective agonist SIOM as examples. The high selectivity of NTI and SIOM for the δ-receptor has been attributed to their hydrophobic benzene moiety attached to the morphinan nucleus. Conformational constraint of this address group is a prerequisite for enhanced selectivity towards the δ opioid receptor. This benzene moiety is conformationally constrained by the pyrrolo scaffold in NTI and by the spirocyclopentano scaffold in SIOM. Selectivity for the δ receptor is enhanced by incorporating a hydrophobic moiety at the morphinan ring position.

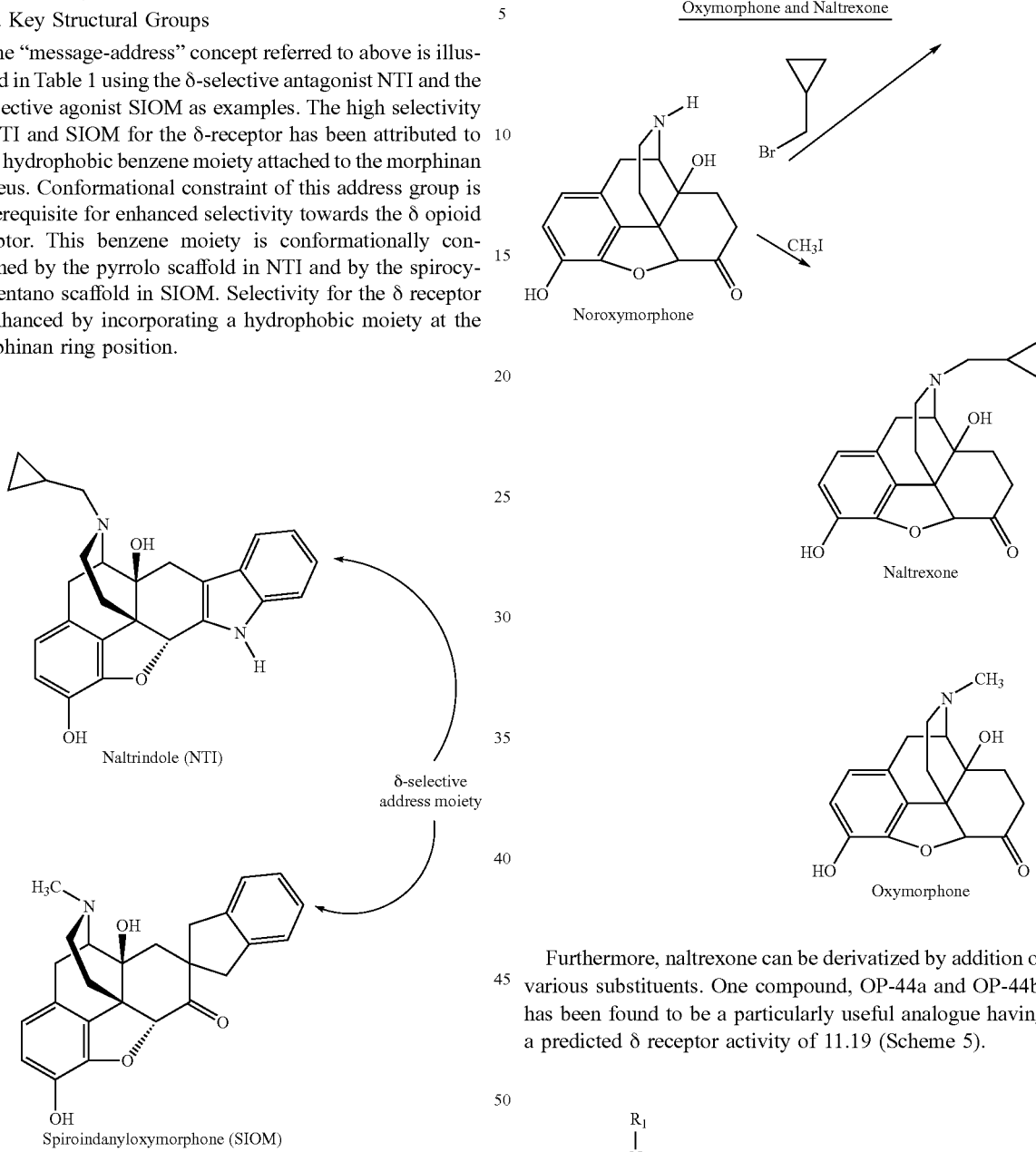

Table 1: Illustration of δ-selective address in two opiods: NTI, a δ-selective antagonist and SIOM, a δ-selective agonist.

B. Synthetic Routes

Generally, the NPOs of the current invention can be synthesized from known opioids by methods known in the art. One starting material, naltrexone, could be used to synthesize a number of compounds of the current invention.

Naltrexone or oxymorphone can be synthesized from noroxymorphone as shown in Scheme 1.

Furthermore, naltrexone can be derivatized by addition of various substituents. One compound, OP-44a and OP-44b, has been found to be a particularly useful analogue having a predicted δ receptor activity of 11.19 (Scheme 5).

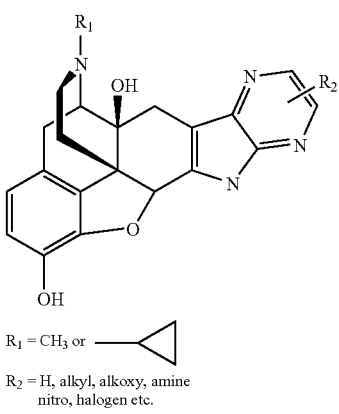

$R_1$ = CH$_3$ or —◁

$R_2$ = H, alkyl, alkoxy, amine nitro, halogen etc.

The derivatization of the naltrexone synthesized by the route shown in Scheme 1, is exemplified in Scheme 2, where OP-39, OP-41 and OP-44 are each synthesized using different functionalities for R.

Further modifications of the NPOs can be accomplished by reacting the intermediate NPO with other reactants to form a variety of substituted or unsubstituted heterocyclic rings. Scheme 3 depicts some possible modifications of OP-44 with variations at the ring labled A. These synthetic schemes can be accomplished by general synthetic methods known in the art.

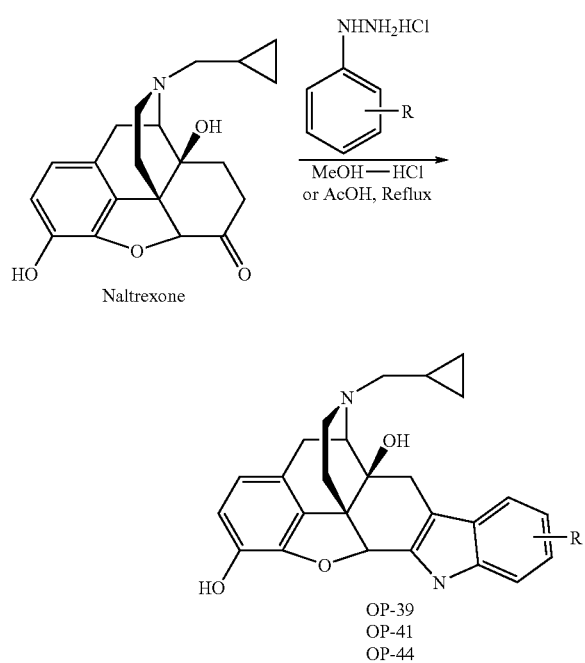

Scheme 2
General Synthetic Scheme of Naltrindole Derivatives

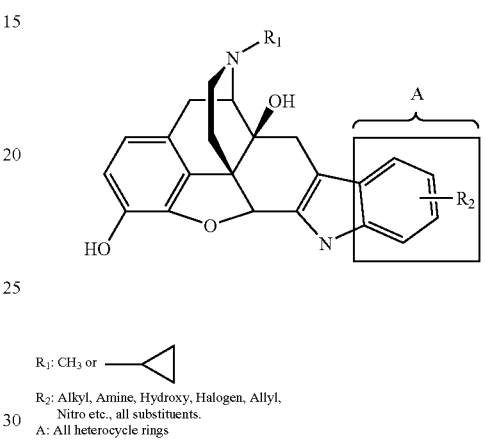

Scheme 3
Possible Modification of OP-44 Derivatives Based on General Synthetic Pathway $R_1$: $CH_3$ or cyclopropylmethyl
$R_2$: Alkyl, Amine, Hydroxy, Halogen, Allyl, Nitro etc., all substituents.
A: All heterocycle rings Other possible synthetic pathways for NPO derivatives structurally similar to OP-26 is shown in Scheme 4 where bromination and addition steps allow for the addition of various functionalities to the NPO.

Scheme 4
Possible Synthetic Pathway of OP-26 Derivatives

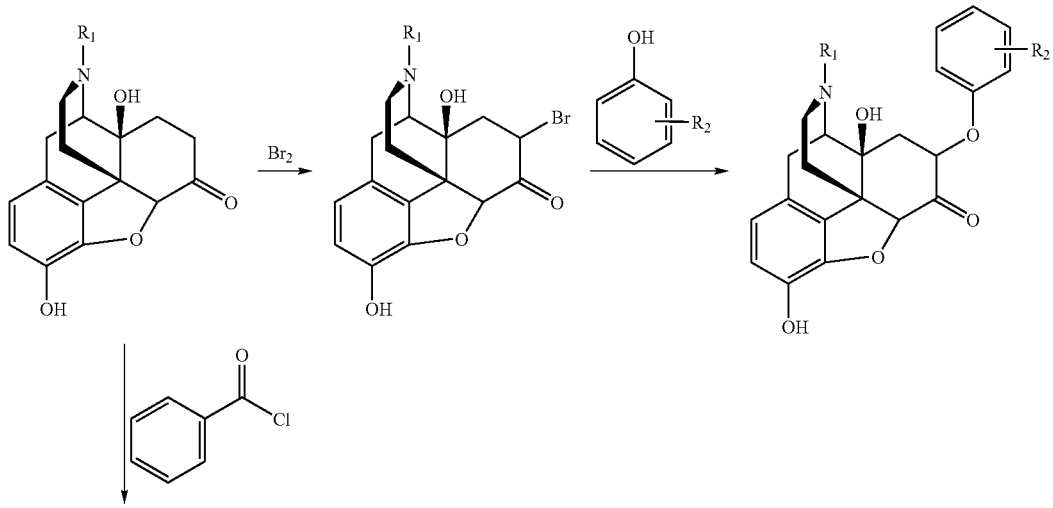

-continued
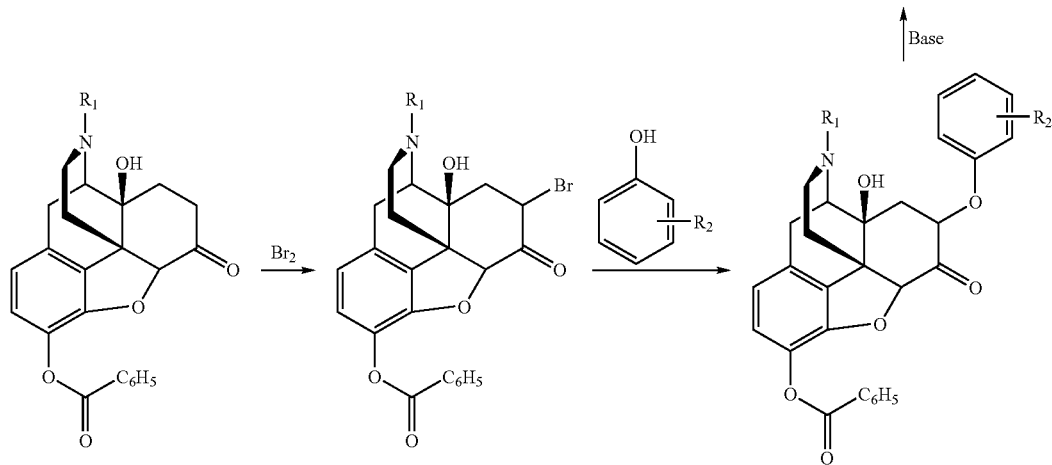
NPO analogues similar to OP-44a and OP-44b can be synthesized by similar methods or as described in Liao et al. (1998); Stevens et al. (2000) and Conn et al. (1990). Scheme 5 summarizes possible synthetic pathways of OP-44a and OP-44b derivatives.
Scheme 5
Summarized Synthetic Pathway of OP-44 derivatives
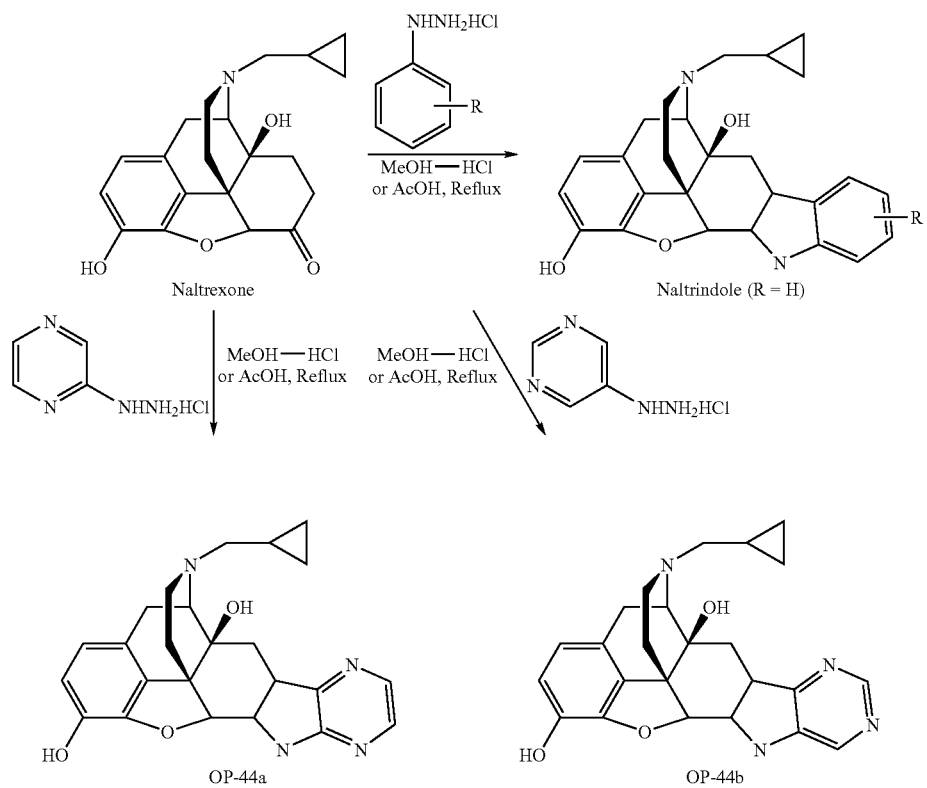

NPO analogues similar to OP-26 can be synthesized by methods such as those described in Scheme 6.

Scheme 6
Possible Synthetic Pathway of OP-44

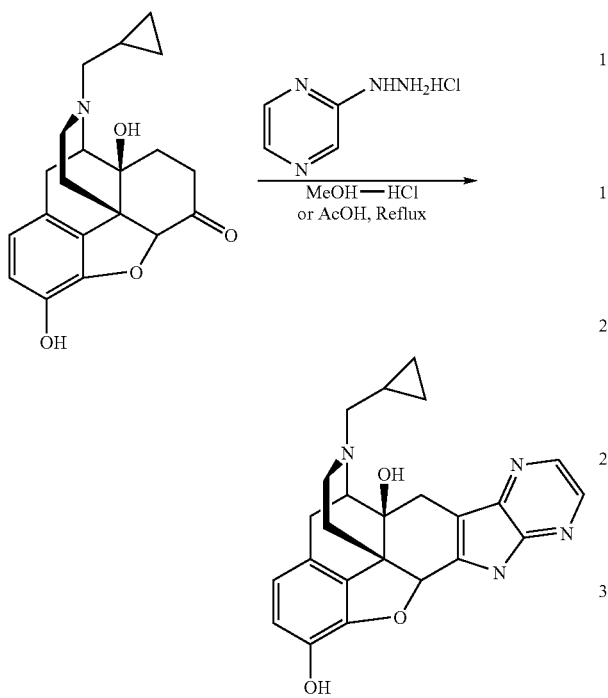

NPOS with hydrazine-HCl salts can be synthesized as described in Scheme 7.

Scheme 7
General Synthetic Pathway of Hydrazine-HCl Salts

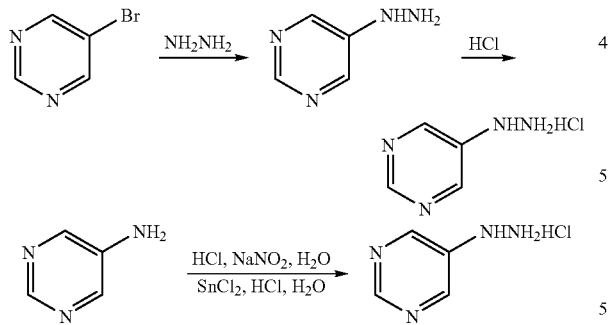

Naltrexone and other starting materials can be prepared and purified by synthetic methods which are well known in the art (Ananthan et al., 1999).

A. Stereochemistry

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase). It is also well known in the art, and for example, as illustrated herein below how to determine opioid receptor activity, for example, δ, μ or κ, or related receptor activity using the standard tests described herein, or using other similar tests.

The stereochemistry of the NPOs is important in that changing the stereocenters affects the activity of the compound (Ohkawa et al., 1998). The effect of stereochemistry for the NPO OP-26 and the saturated derivatives on the activity of the δ receptor was studied. The molecules studied include:

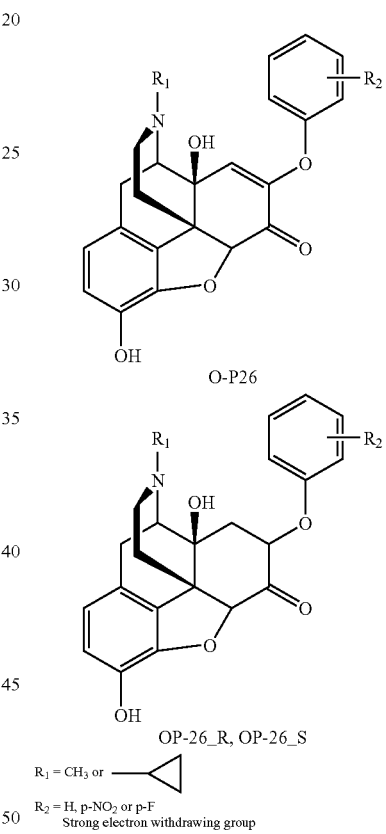

The predicted activity for δ, μ and κ receptors as well as the C log P were determined and are shown in Table 2.

TABLE 2

| Compound | δ receptor | μ receptor | κ receptor | ClogP |
|---|---|---|---|---|
| OP-26 | 10.51 | 7.45 | 6.92 | 1.00 |
| OP-26_R | 9.10 | 6.74 | 6.07 | 0.90 |
| OP-26_S | 10.36 | 6.53 | 6.49 | 0.90 |

As shown in Table 2, the greatest activity for the δ receptor is seen with OP-26, with the R isomer having the lowest activity. The activity towards the μ and κ receptors is also greatly affected by the stereochemistry. Similarly, with compounds OP-3, OP-4, and OP-5, which are all isomers of each other, the greatest predicted activity towards the δ receptor is for the OP-4 which has one R and three S stereocenters.

B. Chemical Definitions

The term "alkyl" refers to the saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyls of the current invention are preferably from between 1 and 20 carbons in length.

The term "linear alkyl" refers to alkyls which have a straight chain, such as n-butane, n-pentane, n-hexane etc.

The term "branched alkyl" refers to alkyls with one or more branch off of the hydrocarbon backbone. Such moieties can include, for example, t-butyl, isopropyl, sec-butyl, etc.

The term "ring system" refers to a composition or part of a composition having two or more connected cyclic moieties. The rings may be comprised of carbon or a combination of carbon, nitrogen, oxygen or sulfur and will have between three and eight members in each ring. The rings may be saturated or unsaturated and may be substituted or unsubstituted.

The term "substituted alkyl" refers to alkyl moieties having moieties replacing a hydrogen on one or more carbons of the hydrocarbon backbone. Such moieties can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the moieties described above. An "aralkyl" moiety is an alkyl substituted with an aryl (e.g., phenylmethyl (benzyl)).

The term "substituted branched alkyl" refers to an alkyl that is both substituted and branched.

As used herein, the term "organic moiety" is intended to include carbon based functional groups such as alkyl, alkylamino, alkoxy, aryl, aralkyl, aryloxy, alkylthio, and alkylcarboxyl.

As used herein, the term "inorganic moiety" is intended to include non carbon-based groups or elements such as hydrogen, halo, amino, nitro, thiol, and hydroxyl.

As used herein, the term "halosubstituted alkyl moieties" is intended to include alkyl moieties which have halogen moieties in the place of at least one hydrogen.

As used herein, the term "nitro" means —$NO_2$; the term "halogen" designates —F, —Cl, —Br or —I; the term "thiol" means —SH; and the term "hydroxyl" means —OH. Thus, the term "alkylamino" as used herein means an alkyl group, as defined above, having an amino group attached thereto. The term "alkylthio" refers to an alkyl group, as defined above, having a sulfhydryl group attached thereto. The term "alkylcarboxyl" as used herein means an alkyl group, as defined above, having a carboxyl group attached thereto.

The term "aromatic group" is intended to include unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylamine, a lower alkylcarbonyl, a nitro, a hydroxyl, —$CF_3$, —CN, or the like.

The term "alkoxy", as used herein, refers to a moiety having the structure —O-alkyl, in which the alkyl moiety is described above.

The term "aryl" as used herein includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such moieties, e.g., as described above for alkyl groups. Preferred aryl groups include unsubstituted and substituted phenyl groups.

The term "aryloxy", as used herein, refers to a group having the structure —O-aryl, in which the aryl moiety is as defined above.

The term "amino," as used herein, refers to —$NH_2$ or an unsubstituted or substituted moiety of the formula —$NR_aR_b$, in which $R_a$ and $R_b$ are each independently, hydrogen, alkyl, aryl, or heterocyclyl, or $R_a$ and $R_b$, taken together with the nitrogen atom to which they are attached, form a cyclic moiety having from 3 to 8 atoms in the ring. Thus, the term "amino" is intended to include cyclic amino moieties such as piperidinyl or pyrrolidinyl groups, unless otherwise stated. An "amino-substituted amino group" refers to an amino group in which at least one of $R_a$ and $R_b$, is further substituted with an amino group.

As used herein the term "agonist" refers to a signaling molecule (hormone, neurotransmitter of synthetic drug) which binds to a receptor, inducing a conformational change which produces a response such as contraction, relaxation, secretion, change in enzyme activity, etc. The term "antagonist" refers to a drug which attenuates the effect of an agonist. Antagonist may be divided either on the basis of being surmountable or insurmountable (synononymous with unsurmountable), or on the basis of being competitive, or non-competitive.

As used herein the specification, "a" or "an" may mean one or more. As used herein in the claim(s), when used in conjunction with the word "comprising", the words "a" or "an" may mean one or more than one. As used herein "another" may mean at least a second or more. As used herein, the term "about" means within 25% of the stated value, or more preferentially within 15% of the value.

VIII. Pharmaceutical Preparations

Pharmaceutical compositions of the present invention comprise an effective amount of one or more opiate analogues disclosed herein and/or an additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human. The preparation of a pharmaceutical composition that contains at least one opiate analogue or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, antioxidants, salts, coatings, surfactants, preservatives (e.g., methyl or propyl p-hydroxybenzoate, sorbic acid, antibacterial agents, antifungal agents), isotonic agents, solution retarding agents (e.g., paraffin), absorbents (e.g., kaolin clay, bentonite clay), drug stabilizers (e.g., sodium lauryl sulphate), gels, binders (e.g., syrup, acacia, gelatin, sorbitol, tragacanth, polyvinylpyrrolidinone, carboxy-methyl-cellulose, alginates), excipients (e.g., lactose, milk sugar, polyethylene glycol), disintegration agents (e.g., agar-agar, starch, lactose, calcium phosphate, calcium carbonate, alginic acid, sorbitol, glycine), wetting agents (e.g., cetyl alcohol, glycerol monostearate), lubricants, absorption accelerators (e.g., quaternary ammonium salts), editable oils (e.g., almond oil, coconut oil, oily esters or propylene glycol), sweetening agents, flavoring agents, coloring agents, fillers, (e.g., starch, lactose, sucrose, glucose, mannitol), tabletting lubricants (e.g., magnesium stearate, starch, glucose, lactose, rice flower, chalk), carriers for inhalation (e.g., hydrocarbon propellants), buffering agents, or such like materials and combinations thereof, as would be known to one of ordinary skill in the art (see, for example, Remington's Pharmaceutical Sciences, 1990, incorporated herein by reference). Except insofar as any conventional carrier is incompatible with the active ingredient, its use in the therapeutic or pharmaceutical compositions is contemplated.

In any case, the composition may comprise various antioxidants to retard oxidation of one or more component. Examples of antioxidants includes ascorbic acid, cysteine hydrochloride, sodium sulfite, sodium bisulfite, sodium metabisulfite, ascorbyl palmitate, butylated hydroxytoluene, butylated hydroxyanisole, lecithin, propyl gallate, and α-tocopherol. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof).

The opiate analogue may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric, hydrobromic, or phosphoric acids; or such organic acids as acetic, oxalic, tartaric, benzoic, lactic, phosphorifc, citric, maleaic, fumaric, succinic, tartaric, napsylic, clavulanic, stearic, or mandelic acid. Salts formed with the free carboxyl groups can also be derived from inorganic bases such as for example, sodium, potassium, ammonium, calcium magnesium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The opiate analogue may also comprise different types of carriers depending on whether it is to be administered in solid or liquid form, and whether it need to be sterile for such routes of administration as injection. The present invention can be administered orally, intradermally, subcutaneously, topically, by injection, infusion, continuous infusion, localized perfusion, bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990, incorporated herein by reference).

The opiate analogue when administered orally may be in the form of tablets, capsules, sachets, vials, powders, granules, lozenges, reconstitutable powders, liquid preparations. The NPO may be admistered via transdermal delivery using a skin-patch formulation. The NPO may be dispersed in a pressure sensitive adhesive which adheres to the skin such that it can diffuse through the skin for delivery to the patient. Transdermal adhesives such as natural rubber or silicone are known in the art.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as a solvent is envisioned to result in extremely rapid penetration, delivering high concentrations of the active agents to a small area.

The actual dosage amount of a composition of the present invention administered to a patient can be determined by physical and physiological factors such as the severity of the pain, body weight, gender, severity of condition, the type of disease being treated, previous or concurrent therapeutic interventions, idiopathy of the patient, time of the administration, rate of excretion of the particular compound, and on the route of administration. The practitioner responsible for administration will, in any event, determine the concentration of active ingredient(s) in a composition and appropriate dose(s) for the individual subject. The dosage will also depend upon the bioavailability and activity of the particular NPO.

In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Administration of opioids in the epidural or intrathecal space provides more direct access to the first pain-processing synapse in the dorsal horn of the spinal cord. This permits the use of doses substantially lower than those required for oral or parenteral administration, and may be used in the current invention since systemic side effects are thus decreased. However, epidural opioids have their own dose-dependent side effects, such as itching, nausea, vomiting, respiratory depression, and urinary retention. As a consequence, after intraspinal administration, delayed respiratory depression can be observed. While the risk of delayed respiratory depression is reduced with more lipophilic opioids it is not removed. Extreme vigilance and appropriate monitoring is required for all patients receiving intraspinal narcotics. Nausea and vomiting are also more prominent symptoms with intraspinal opioids. However, supraspinal analgesic centers can also be stimulated, possibly leading to synergistic analgesic effects.

Analogous to the relationship between systemic opioids and NSAIDS, intraspinal narcotics are often combined with local anesthetics. This permits the use of lower concentrations of both agents, minimizing local anesthetic complications of motor blockade and the opioid induced complications listed above. Epidural administration of opioids have become popular in the management of postoperative pain, and for providing analgesia for labor and delivery. Lower systemic opioid levels are achieved with epidural opioids, leading to less placental transfer and less potential for respiratory depression of the newborn (Schnider and Levinson 1987). Intrathecal ("spinal" anesthesia) administration of opioids as a single bolus is also popular for acute pain management.

IX. Combination Therapy

It is an aspect of this invention that the opiate analogue can be used in combination with another agent, such as an opioid or other theraputic agent. The opiate analogue may precede or follow the other agent treatment by intervals ranging from minutes to weeks. In other aspects, one or more agents may be administered within from about 1 minute, about 5 minutes, about 10 minutes, about 20 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the opiate analogue. In certain other embodiments, an agent may be administered within from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the opiate analogue. In some situations, it may be desirable to extend the time period for treatment significantly, however, where several weeks (e.g., about 1, about 2, about 3, about 4, about 5, about 6, about 7 or about 8 weeks or more) lapse between the respective administrations.

Various combinations may be employed, where the opiate analogue is "A" and the secondary agent is "B":

A/B/A B/A/B B/B/A A/A/B A/B/B B/A/A A/B/B/B B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the therapeutic expression constructs of the present invention to a patient will follow general protocols for the administration of opioids, taking into account the toxicity, if any, of the vector. It is expected that the treatment cycles would be repeated as necessary. It also is contemplated that various standard therapies, as well as surgical intervention, may be applied in combination with the described opiod therapy.

Opioid analgesics that can be used in conjugation with the opiate analogue of the current invention include, but are not limited to morphine, morphine sulphate, tramadol, codeine, levorphanol, meperidine and congeners such as diphenoxylate and loperaminde, sufentanil citrate and congeners such as alfentanil and remifentanil, methadone and congeners, levomethadyl acetate (LAAM), propoxyphene, butorphanol, eptazocine, fentanyl, fentanyl citrate, flupirtine, hydromorphone and oxycodone. Other opioid compounds that may be used include, but are not limited to pentazocine, nalbuphine, butorphanol, buprenorphine, meptazinol, dezocine, nalorphine, levallorphan and nalmefene, morphine-6-glucuronide, morphine (DepoMorphine, AERx Pain Management System, Multipor technology), morphine sulphate, pulmonary-delivered morphine sulphate, and other morphine-like compounds including conorfone, propiram fumarate, various strength opioid analgesics using OROS technology, various strength analgesics using Geomatrix technology, fentanyl, AERx Pain Management System, buprenorphine, asimadoline, TRK-820, LEF (BCH-3963), loperamide, oxycodone and oxycodone combinations (i.e. oxycodone+ibuprofen or oxycodone+paracetamol), DPI-3290, ADL-10-

0101, Xorphanol, TSN-09, and a combination of NMDA antagonist and an opioid compound, (i.e. dextromethorphan+hydrocodone, dextromethorphan+morphine and dextromethorphan+oxycodone+paracetamol) ("Advances in Pain Management," Scrip Reports, February 2000).

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Three Dimensional Structure-Activity Relationship (3D-QSAR) Models

The inventors employed approaches in computer-aided molecular design (CAMD) to develop 3-dimensional quantitative structure-activity relationship (3D-QSAR) molecular models based on a series of known opioids for which experimental binding data are available (Raynor et al., 1994). These 3D-QSAR models were used as tools to guide the design of novel, more potent, molecules and to predict their biological activity prior to the time-consuming chemical synthesis and biological testing of all possible candidates. By using 3D-QSAR models to filter or screen out the less active candidates, resources can be focused on the most promising candidates thereby accelerating the drug discovery process.

Initial structural geometries were obtained from the published x-ray crystal structures of several opioids included in this study. Each molecular structure was geometrically optimized within the Sybyl molecular modeling program (Tripos Inc., St. Louis, Mo.). Separate 3D-QSAR models were constructed for the three types of opioid receptors ($\delta$, $\kappa$, and $\mu$), thus providing a tool for rational design of novel $\delta$-specific candidates. To build these 3D-QSAR models, two independent techniques were employed: CoMFA (Comparative Molecular Field Analysis) (Cramer III et al., 1988), accessed through the Sybyl program, and MFA (Molecular Field Analysis) accessed through the Cerius$^2$ program (Molecular Simulations, Inc., San Deigo, Calif.). CoMFA and MFA are independent yet highly complementary, thus results from each approach served as an internal check on the computational methodology.

After establishing the statistical validity, these 3D-QSAR models were employed as tools to guide the design of novel molecules and to predict their biological activity prior to chemical synthesis (thus saving tremendous time and expense). Based on these 3D-QSAR models, "pharmacophoric maps" were constructed that identify those key structural groups responsible for conferring receptor affinity and selectivity and that visually depict the relative orientation of these key groups in 3D space. Using this knowledge, a large number of (>150) of novel $\delta$-selective molecules were computer-designed representing structural analogues of the well-known opioids morphine (a $\mu$-selective agonist), NTI (a $\delta$-selective antagonist), and SIOM (a $\delta$-selective agonist) (FIG. 1). These novel molecules exhibit much improved bioavailability compared with NTI and SIOM. The bioavailability of a pharmaceutical drug relates to the rate and extent of the active ingredient that reaches the systemic circulation. To estimate the bioavailability of each compound, the so-called log P that provides a measure of the molecule's hydrophobic-hydrophilic balance was calculated.

Results from CoMFA and MFA models yielded nearly identical conclusions, therefore only the CoMFA results are presented herein. Separate CoMFA models were constructed for the $\delta$, $\kappa$, and $\mu$ opioids based on published binding data (Raynor et al., 1994). The results for the $\delta$, $\kappa$, and $\mu$ opioids are summarized in FIG. 2A, FIG. 2B, and FIG. 2C, respectively, as plots of the CoMFA-predicted vs. experimentally observed values of the binding affinity (given as $pK_I$). In all three cases, the 3D-QSAR models exhibited exceptional statistical self-consistency ($r^2>0.90$) and internal predictive ability ($r_{cv}^2>0.60$). The regression equations corresponding to these correlation plots served as tools for predicting the binding affinity of novel molecules.

Figure 3:
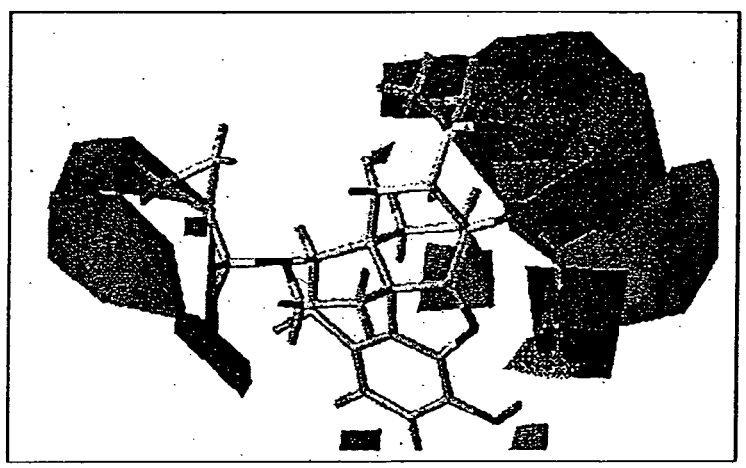
FIG. 3. Steric-electrostatic pharmacophore contour map for the δ opioid receptor based on the CoMFA model. The structure of the opioid diprenorphin is shown for reference.

One of the unique features of CoMFA is its ability to represent the 3D-QSAR models visually as steric-electrostatic pharmacophore maps, as shown in FIG. 3 for the $\delta$-selective opioids. These CoMFA contour maps were used as visual guides for designing novel $\delta$-selective molecules. Green-colored polygons denoted regions where increased steric bulk (i.e., additional chemical groups) is favorable for enhanced $\delta$ opioid activity, whereas yellow polygons denoted regions where decreased steric bulk (i.e., fewer chemical groups) is favorable for enhanced $\delta$ opioid activity. Likewise, the red polygons denoted regions where negative electrostatic charge (e.g., from acidic groups) is favorable while the yellow polygons denoted regions where positive electrostatic charge (e.g., from basic groups) is favorable for enhance $\delta$ opioid activity. This information provided information in designing molecules that exhibited both high binding affinity and high selectivity for the $\delta$ opioid receptor.

Example 2

Design of Novel $\delta$-Selective Opioids: Analogues of NTI and SIOM

Figure 4:
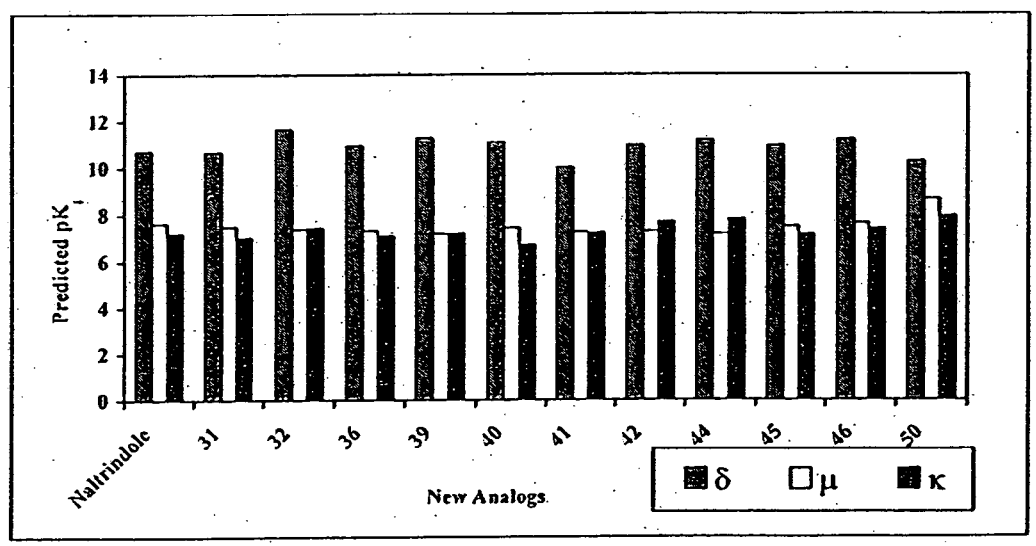
FIG. 4. Histograms comparing predicted binding affinities of selected new candidates for the δ, κ, and μ opioid receptors: NTI analogues.
Figure 5:
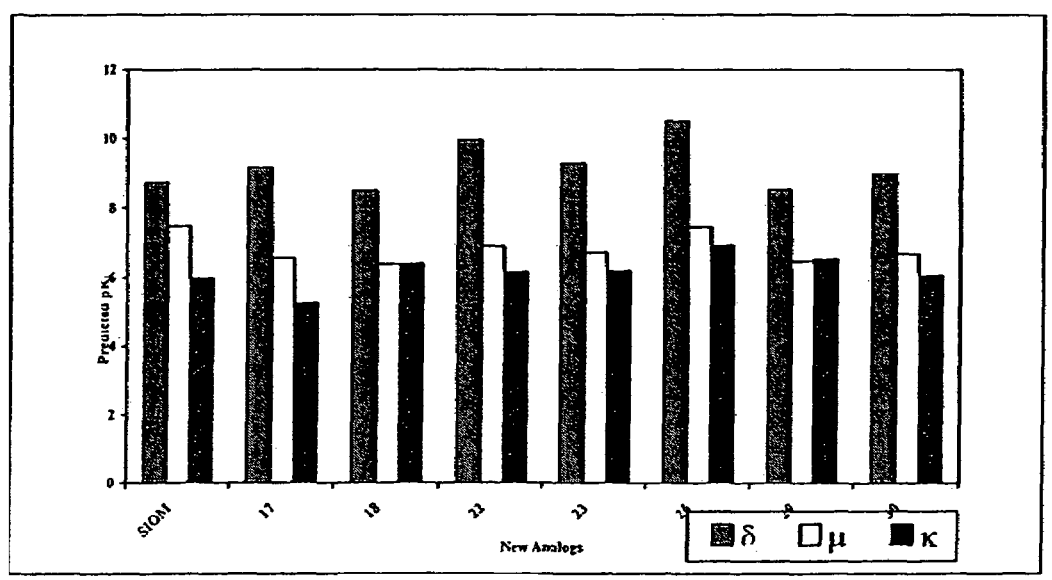
FIG. 5. Histograms comparing predicted binding affinities of selected new candidates for the δ, κ, and μ opioid receptors: SIOM analogues.

Using the 3D-QSAR models and pharmacophoric maps, a large number of novel NTI and SIOM analogs (>100) that retain or exceed the $\delta$-receptor affinity and selectivity of NTI and SIOM yet exhibit improved bioavailability, were computer-designed. The binding affinities ($pK_1$) of these novel molecules, for all three opioid receptors ($\delta$, $\kappa$, and $\mu$), were predicted using the appropriate 3D-QSAR model. The results for a subset of these novel molecules are summarized in FIG. 4 for the NTI analogues and in FIG. 5 for the SIOM analogues. Many of these novel compounds are predicted to exhibit equal or superior binding affinity and selectivity for the $\delta$ receptor compared with NTI (far left in FIG. 4) and SIOM (far left in FIG. 5). It should be noted that both NTI (a $\delta$ antagonist) and SIOM (a $\delta$ agonist) possess high binding affinity and high selectivity for the $\delta$ opioid receptor.

Figure 6:
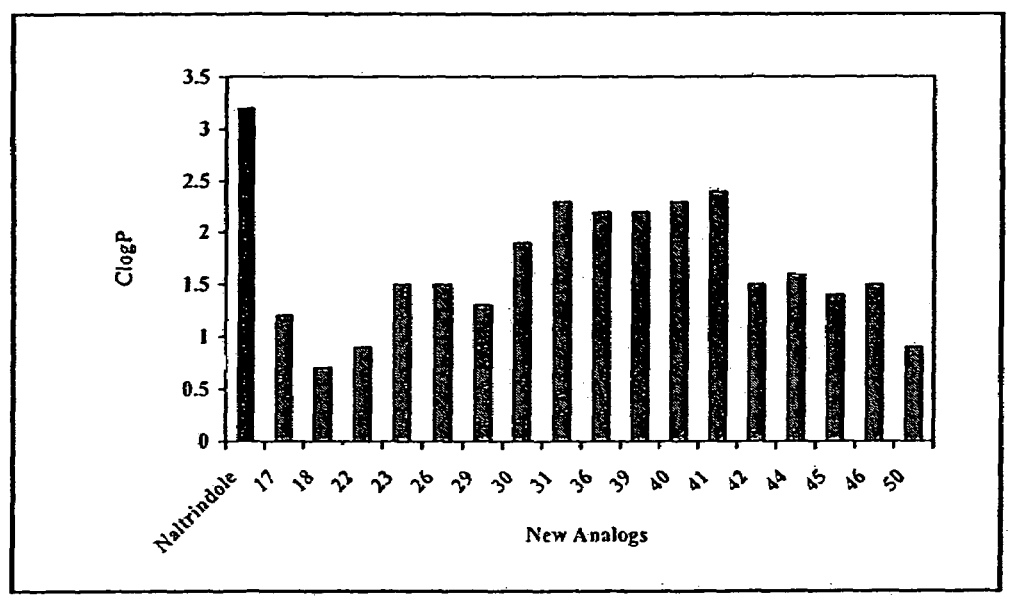
FIG. 6. Calculated log P values for selected novel compounds vs. NTI.

The $\delta$-receptor binding affinity and selectivity of these NTI and SIOM analogs was either maintained or improved while significantly improving bioavailability. This is illustrated in FIG. 6, where the calculated log P values (C log P) of selected novel compounds are given vs. NTI (log P=3.3).

Preferred NTI and SIOM analogs and their receptor affinities are shown in Table 3 and Table 4 respectively. The structures of compounds 1–20 are nonlimiting examples for the current invention.

TABLE 3

Newly Designed Opioid Analogs and Their Predicted Activity Against δ, μ and κ Receptors with Different Models

| No. | Structure | Predicted Activity | | | Clog P |
|---|---|---|---|---|---|
| | | δ receptor | μ receptor | κ receptor | |
| NTI | 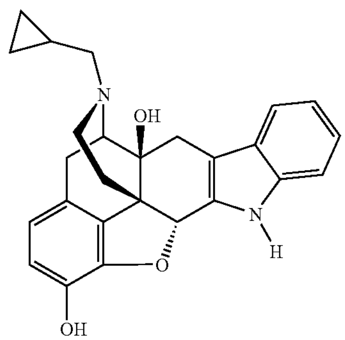 | 10.76 (10.70)# | 7.19 (7.19)# | 7.19 (7.18)# | 2.65 |
| 1 | 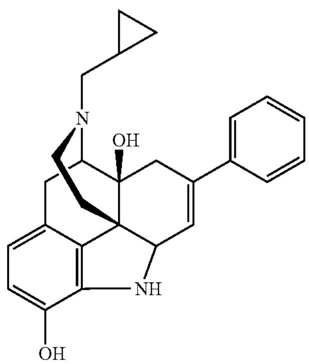 | 10.41 | 7.96 | 7.81 | 3.2 |
| 2 | 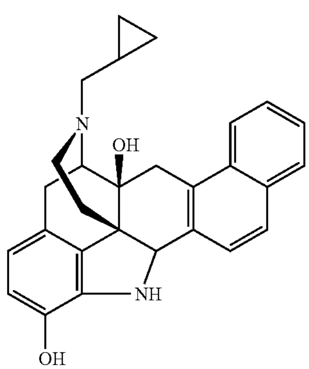 | 10.94 | 7.43 | 7.17 | 3.6 |
| 3 | 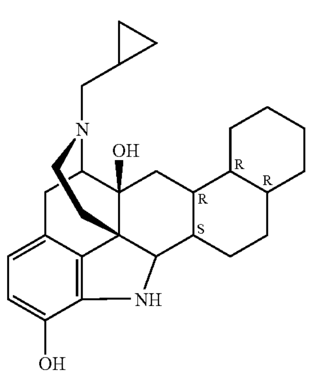 | 9.56 | 8.37 | 9.01 | 4.7 |

TABLE 3-continued

Newly Designed Opioid Analogs and Their Predicted Activity
Against δ, μ and κ Receptors with Different Models

| No. | Structure | Predicted Activity | | | Clog P |
|---|---|---|---|---|---|
| | | δ receptor | μ receptor | κ receptor | |
| 4 | 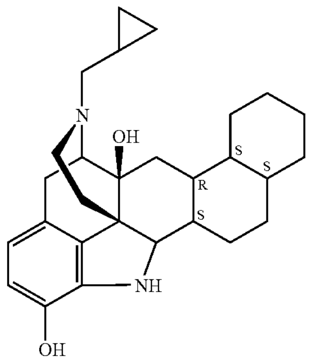 | 10.23 | 8.12 | 8.11 | 4.7 |
| 5 | 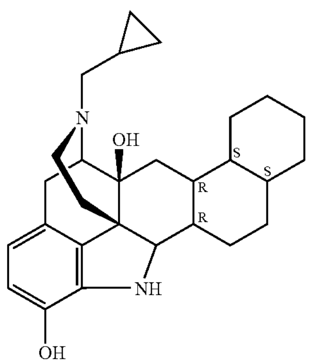 | 9.52 | 8.08 | 7.36 | 4.7 |
| 6 | 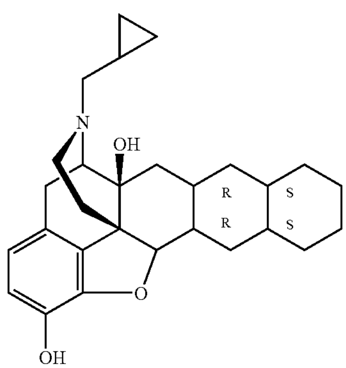 | 9.24 | 9.18 | 10.41 | 4.7 |
| 7 | 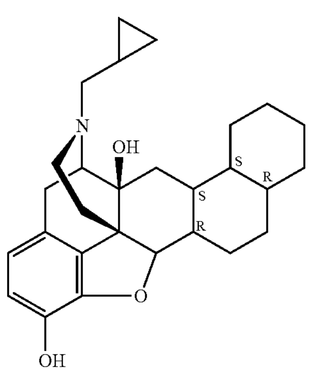 | 9.57 | 8.00 | 6.89 | 5.3 |

TABLE 3-continued

Newly Designed Opioid Analogs and Their Predicted Activity
Against δ, μ and κ Receptors with Different Models

| No. | Structure | Predicted Activity | | | Clog P |
|---|---|---|---|---|---|
| | | δ receptor | μ receptor | κ receptor | |
| 8 | 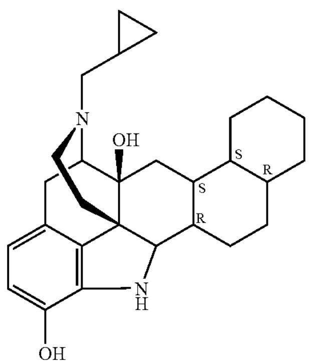 | 9.45 | 8.08 | 6.97 | 4.7 |
| 9 | 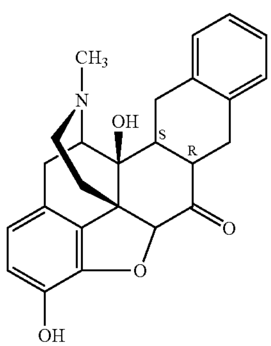 | 9.23 | 6.81 | 5.26 | 2.0 |
| 10 | 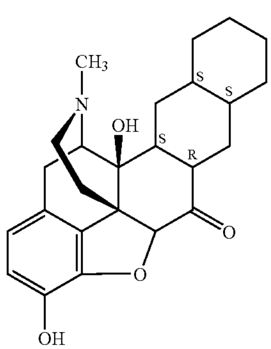 | 7.86 | 8.15 | 6.22 | 2.9 |

Values in parenthesis are the corresponding experimental affinities of NTI (Naltrindole) against the three receptors

TABLE 4

Newly Designed Opioid Analogs and Their Predicted Activities Against δ, μ and κ Receptors

| No. | Structure | Predicted Activity | | | Clog P |
|---|---|---|---|---|---|
| | | δ receptor | μ receptor | κ receptor | |
| SIOM | 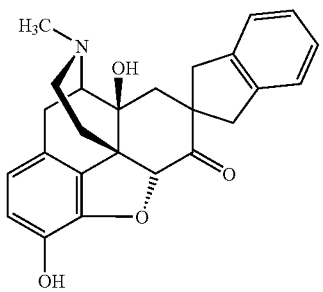 | 8.74 (8.77)# | 7.47 (7.48)# | 6.02 (<6.00)# | 1.5 |
| 11 | 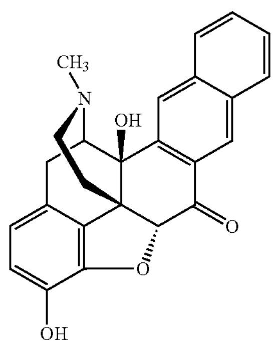 | 8.21 | 6.72 | 6.40 | 2.2 |
| 12 | 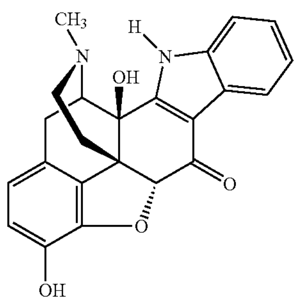 | 8.08 | 6.06 | 4.64 | 1.4 |
| 13 | 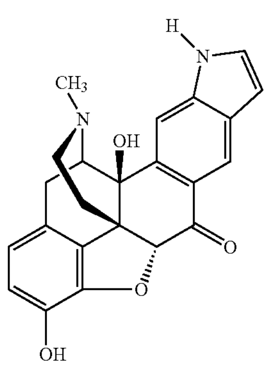 | 8.21 | 6.64 | 6.40 | 1.3 |

TABLE 4-continued

Newly Designed Opioid Analogs and Their Predicted Activities
Against δ, µ and κ Receptors

| | | Predicted Activity | | | |
|---|---|---|---|---|---|
| No. | Structure | δ receptor | µ receptor | κ receptor | Clog P |
| 14 | | 8.14 | 6.69 | 6.44 | 1.6 |
| 15 | | 8.20 | 6.63 | 6.41 | 1.6 |
| 16 | | 8.67 | 6.82 | 6.07 | 1.2 |
| 17 | | 9.17 | 6.57 | 5.25 | 1.2 |

TABLE 4-continued

Newly Designed Opioid Analogs and Their Predicted Activities Against δ, μ and κ Receptors

| No. | Structure | Predicted Activity | | | Clog P |
|---|---|---|---|---|---|
| | | δ receptor | μ receptor | κ receptor | |
| 18 | | 8.49 | 6.38 | 6.39 | 0.7 |
| 19 | | 8.34 | 6.57 | 6.26 | 1.3 |
| 20 | | 8.43 | 6.44 | 6.05 | 0.4 |

Values in parenthesis are the corresponding experimental affinities of SIOM against the three receptors.

Use of 3D-QSAR mapping resulted in a pharmacophoric map of δ-selective compounds of which the structure of compounds 21–50 are list in Table 5 and compounds 68–70 are listed in Table 6.

TABLE 5

Opioid Analogs and Their Predicted Activities Against δ, μ and κ Receptors

| No. | Structure | Predicted Activity | | | Clog P |
|---|---|---|---|---|---|
| | | δ receptor | μ receptor | κ receptor | |
| 21 | 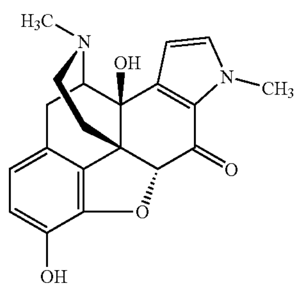 | 7.83 | 6.87 | 6.23 | 0.24 |
| 22 | 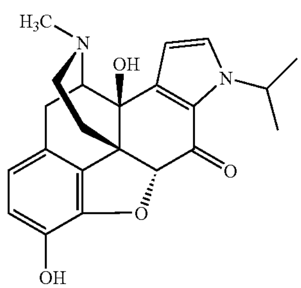 | 9.95 | 6.90 | 6.16 | 0.94 |
| 23 | 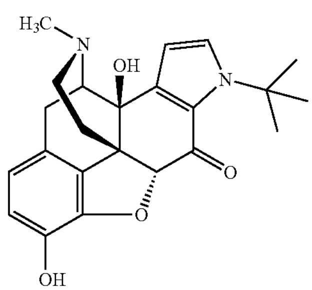 | 9.29 | 6.72 | 6.20 | 1.48 |
| 24 | 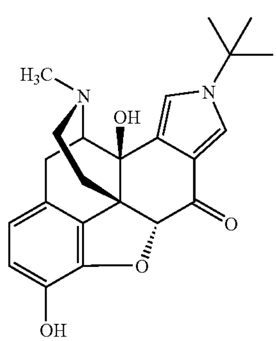 | 8.25 | 6.41 | 6.32 | 1.48 |

TABLE 5-continued

Opioid Analogs and Their Predicted Activities Against δ, μ and κ Receptors

| No. | Structure | Predicted Activity | | | Clog P |
|---|---|---|---|---|---|
| | | δ receptor | μ receptor | κ receptor | |
| 25 | | 8.35 | 6.90 | 5.86 | 1.38 |
| 26 | | 10.51 | 7.45 | 6.92 | 1.46 |
| 27 | | 8.49 | 7.19 | 6.95 | 2.82 |
| 28 | | 7.58 | 6.73 | 5.87 | 2.00 |

TABLE 5-continued

Opioid Analogs and Their Predicted Activities Against δ, μ and κ Receptors

| No. | Structure | Predicted Activity | | | Clog P |
| --- | --- | --- | --- | --- | --- |
| | | δ receptor | μ receptor | κ receptor | |
| 29 | 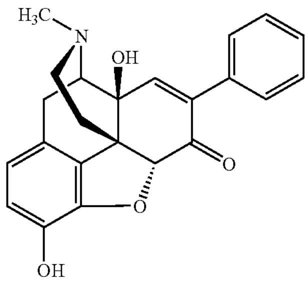 | 8.52 | 6.47 | 6.54 | 1.28 |
| 30 | 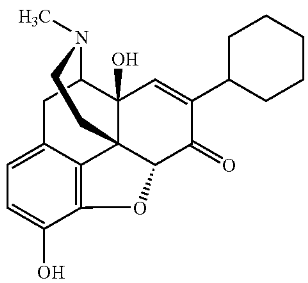 | 9.16 | 6.69 | 6.06 | 1.90 |
| 31 | 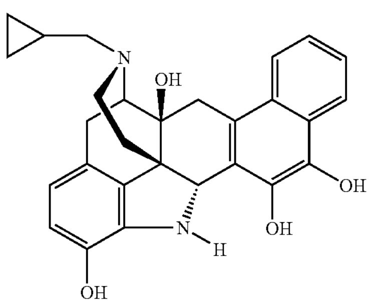 | 10.67 | 7.49 | 7.04 | 2.33 |
| 32 | 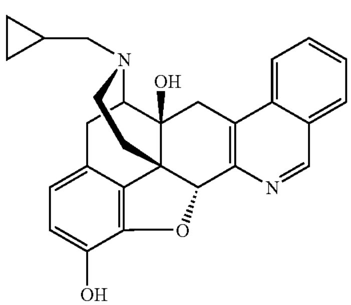 | 11.65 | 7.38 | 7.44 | 2.91 |
| 33 | 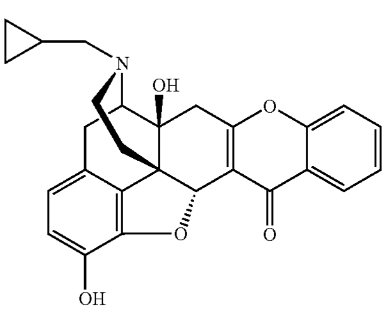 | 9.07 | 8.69 | 8.01 | 2.47 |

TABLE 5-continued

Opioid Analogs and Their Predicted Activities Against δ, μ and κ Receptors

| No. | Structure | Predicted Activity | | | Clog P |
|---|---|---|---|---|---|
| | | δ receptor | μ receptor | κ receptor | |
| 34 | | 6.85 | 7.83 | 7.32 | 1.90 |
| 35 | | 11.98 | 7.38 | 6.73 | 3.41 |
| 36 | | 10.94 | 7.32 | 7.11 | 2.24 |
| 37 | | 11.49 | 8.50 | 6.91 | 4.26 |
| 38 | | 11.53 | 7.09 | 7.28 | 2.88 |

TABLE 5-continued

Opioid Analogs and Their Predicted Activities Against δ, μ and κ Receptors

| No. | Structure | Predicted Activity | | | Clog P |
|---|---|---|---|---|---|
| | | δ receptor | μ receptor | κ receptor | |
| 39 | 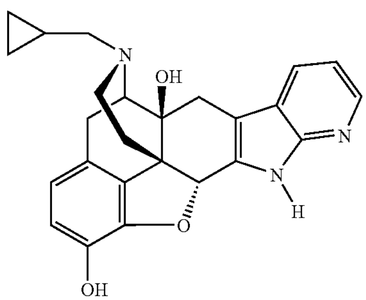 | 11.28 | 7.20 | 7.20 | 2.26 |
| 40 | 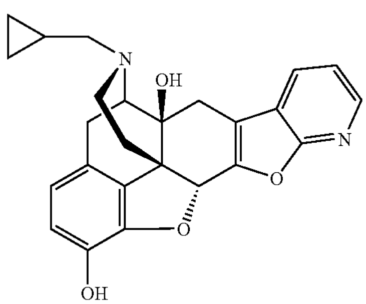 | 11.10 | 7.43 | 6.70 | 2.29 |
| 41 | 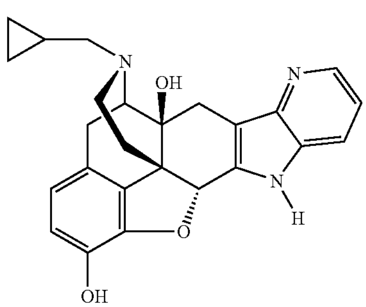 | 10.02 | 7.27 | 7.23 | 2.47 |
| 42 | 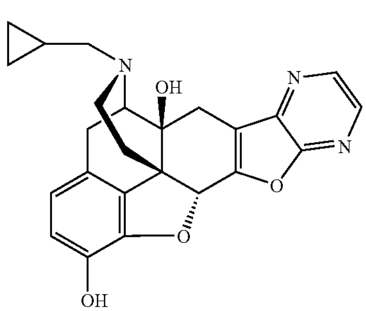 | 10.95 | 7.30 | 7.68 | 1.55 |

TABLE 5-continued

Opioid Analogs and Their Predicted Activities Against δ, µ and κ Receptors

| No. | Structure | Predicted Activity | | | |
| --- | --- | --- | --- | --- | --- |
| | | δ receptor | µ receptor | κ receptor | Clog P |
| 43 | 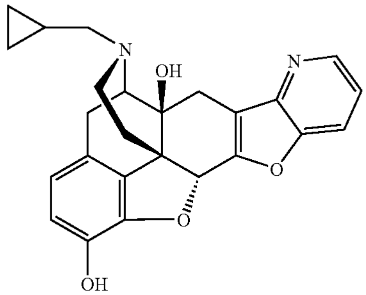 | 10.67 | 8.33 | 8.54 | 2.50 |
| 44 | 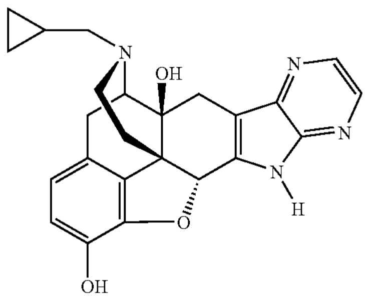 | 11.19 | 7.19 | 7.82 | 1.68 |
| 45 | 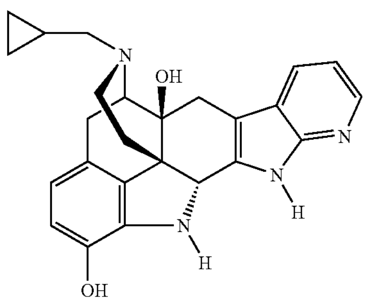 | 10.93 | 7.49 | 7.16 | 1.46 |
| 46 | 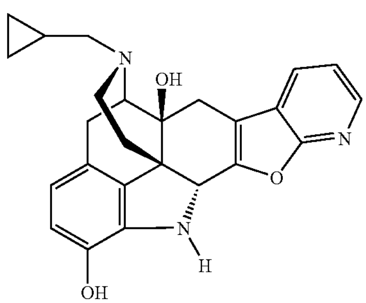 | 11.21 | 7.63 | 7.39 | 1.49 |
| 47 | 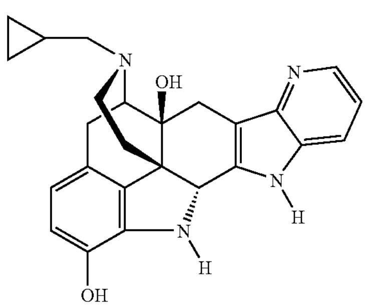 | 10.28 | 8.04 | 7.72 | 1.67 |

TABLE 5-continued

Opioid Analogs and Their Predicted Activities Against δ, μ and κ Receptors

| No. | Structure | Predicted Activity | | | |
|---|---|---|---|---|---|
| | | δ receptor | μ receptor | κ receptor | Clog P |
| 48 | 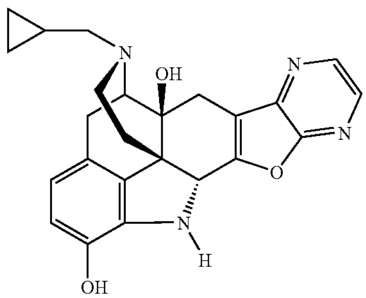 | 10.48 | 8.75 | 7.91 | 0.74 |
| 49 | 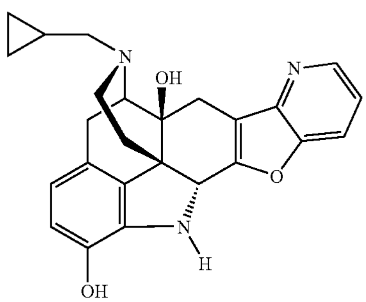 | 11.10 | 7.49 | 7.95 | 1.70 |
| 50 | 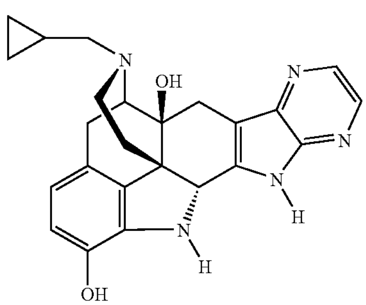 | 10.27 | 8.66 | 7.94 | 0.87 |

TABLE 6

Opioid Analogs and Their Predicted Activities Against δ, μ and κ Receptors

| No. | Structure | Predicted Activity | | | |
|---|---|---|---|---|---|
| | | δ receptor | μ receptor | κ receptor | Clog P |
| 68 | 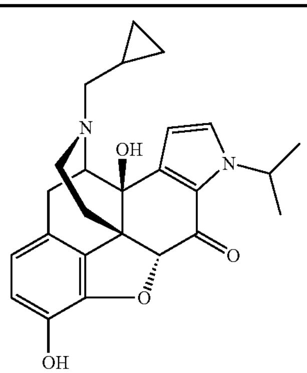 | 8.44 | 7.87 | 7.72 | 1.9 |

TABLE 6-continued

Opioid Analogs and Their Predicted Activities Against δ, μ and κ Receptors

| No. | Structure | Predicted Activity | | | |
|---|---|---|---|---|---|
| | | δ receptor | μ receptor | κ receptor | Clog P |
| 69 | 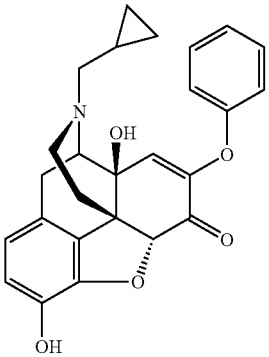 | 9.66 | 7.64 | 7.08 | 2.3 |
| 70 | 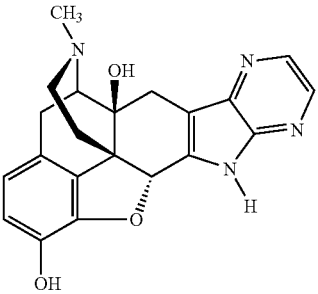 | 10.21 | 6.16 | 6.22 | 0.9 |

Example 3

Chemical Synthesis

The synthesis of SIOM-based analog, OP-26 is given in Scheme 4. The synthesis of naltrindole-based analogs (OP-44 derivatives) is provided in Scheme 5.

Example 4

Biological Evaluation of Delta Opioid-Receptor Affinity and Selectivity

In vivo studies using animal models will be carried out on the compounds of the current invention having high bioavailability. Compounds such as OP-44a and OP-44b which may have high bioavailability will be subject to testing using rat or other animal models for example as described in U.S. Pat. No. 5,922,887 and U.S. Pat. No. 6,359,111.

Example 5

Pharmaceutical Dosage Forms

The following illustrate representative pharmaceutical dosage forms, containing a compound of the invention ('Compound X'), such as Formula I or II for therapeutic or prophylactic use in humans.

| (i) Table 1 | Mg/tablet |
|---|---|
| 'Compound X' | 100.0 |
| Lactose | 77.5 |
| Providone | 15.0 |
| Croscarmellose sodium | 12.0 |
| Microcrystalline cellulose | 92.5 |
| Magnesium stearate | 3.0 |
| | 300.00 |

| (ii) Table 2 | Mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | Mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | Mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s |
| Water for injection | q.s ad 1 mL |

| (v) Injection 2 (10 mg/ml) | Mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s ad 1 mL |

| (vi) Aerosol | Mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

Example 6

DST Analogue (DST3-2)

As demonstrated in Table 7 and FIG. 7, the opoid, DST analogue (DST3-2) was found to exhibit reasonably high delta binding affinity (140 nM) and good delta/mu selectivity (~10/1). One particular feature noted about DST3-2 is that it exhibits good activity even thought it lacks a basic nitrogen common to virtually all opioid receptor active compounds. Currently, the derivative which contains the basic nitrogen group [$R3=-N(CH_3)_2$] is been synthesized.

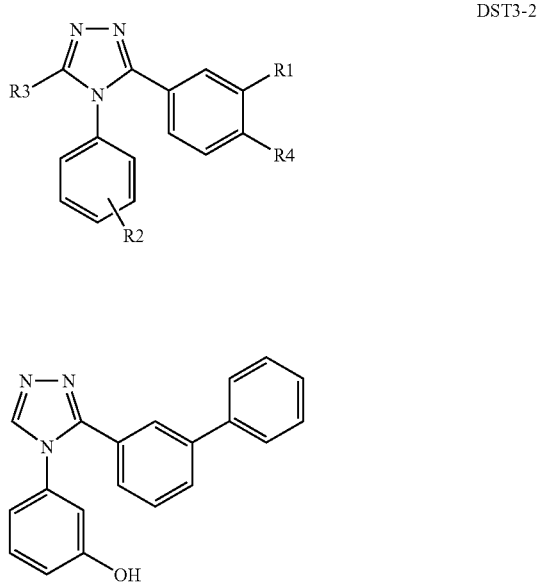

TABLE 7

| | R1 | R4 | R2 | R3 | MW | % Inhibition[a] | | | Representative $K_i$[a] | |
|---|---|---|---|---|---|---|---|---|---|---|
| | | | | | | δ | μ | κ | δ | μ |
| DST3-2 | phenyl | H | meta-OH | H | 313 | 84 | 84 | 42 | 140 nM[b] | 1000 nM[b] |

[a]Competitive analysis; reference compound $^3$H-Bremazocine
[b]Dose response curves shown in FIG. 7.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,816,586
U.S. Pat. No. 5,298,622
U.S. Pat. No. 5,457,208
U.S. Pat. No. 5,922,887
U.S. Pat. No. 6,359,111
Abdelhamid et al., *J. Pharmacol. Exp. Ther.*, 258:299, 1991.
Akil et al., *Annual Rev. Neurosci.*, 7:223–255, 1984.
Ananthan et al., *J. Med. Chem.*, 41:15, 2872–2881, 1998.
Ananthan et al., *J. Med. Chem.*, 42:18:3527–3538. 1999.
Bertolucci et al., *Neurosci. Abstr.*, 18L1368, 1992.
Blisky et al., *J. Pharmacol. Exp. Ther.*, 273:359, 1995.
Bradbury et al., *Nature*, 260:165, 1976.
Conn et al., *J. Org. Chem.*, 55:90, 2908–13, 1990.
Coombs et al., *Anesthesiology*, 62:358–363, 1985.
Cramer III et al., *J. of the Am. Chem. Soc.*, 110, 5959–67, 1988.
Dressman and Lennernas, In: *Oral Drug Absorption: Prediction and Assessment* (*Drugs and the Pharmaceutical Sciences*), Vol. 106, 2000
Foley, In: *Handbook of Experimental Pharmacology*, Herz (Ed.), Vol. 104/II: Opioids II., Springer-Verlag, Berlin, 693–743, 1993.
Gomez-Flores and Weber, *Immunopharm.*, 48:145–156, 2000.
Hardman and Limbird, In: *Goodman & Gilman's The Pharmacological Basis of Therapeutics*, 10$^{th}$ ed., McGraw-Hill Professional Publishing, 2001.
House et al., *Neurosci. Lett.*, 198:119, 1995.
Hughes et al., *Nature*, 258: 577–579:1975.
Kaliszan et al., *Pure Appl. Chem.*, 73:1465–1475, 2001.
Knapp et al., *Eur J Pharmacol.* 291(2):129–134, 1995.
Knapp et al., *J. Pharmacol. Exp. Ther.*, 277(3):1284–1291, 1996.
Koob et al., *TINS*, 15:186–91, 1992.
Liao et al., *J. Med. Chem.*, 41(24):4767–76, 1998.
Loh et al., *Annu. Rev. Pharmacol. Toxicol.*, 30:123, 1990.
Lutz and Pfister, *J. Receptor Res.*, 12:267, 1992.
Martin, *Pharmacol. Rev.*, 35, 283, 1983.
Olson et al., *Peptides*, 10:1253, 1988.
PCT Appln. WO 99/67203
PCT Appln. WO 99/67206
Pert and Snyder, *Science*, 179:1011–1014, 1973.
Pfeiffer et al., *Science*, 233:774–776, 1986.
Plobeck et al., *J. Med Chem.*, 43:3887–94, 2000.
Portoghese et al, *J. Med. Chem.*, 41:4177–4180, 1998.
Portoghese et al., *J. Med. Chem.*, 36:179–180, 1993.
Raynor et al., *Molecular Pharmacol.*, 45:330, 1994.
Reid et al., *Life Sci.*, 52, PL67, 1993.
Remington's Pharmaceutical Sciences, 18th Ed. Mack Printing Company, 1289–1329, 1990.
Saltzman, In: *Drug Delivery: Engineering Principles for Drug Therapy* (*Topics in Chemical Engineering*) Oxford University Press, 2001.
Schiller et al., *J. Med Chem.*, 42:3520, 1999.
Schnider and Levinson, In: *Anesthesia for Obsterics*, Williams & Wilkins, Baltimore, 566, 1987.
Sharp and Yaksh, *Nat. Med.* 3(8):831–832, 1997.
Simon, *Medicinal Res. Rev.*, 11:357, 1991.
Stevens et al., *J. Med. Chem.*, 43:14:2759–2769, 2000.
Takemori and Portoghese, *Annu. Rev. Pharmacol. Toxicol.*, 32:239–269, 1992.
Wei et al., *J. Med Chem.*, 43:21:3895–905, 2000.

What is claimed is:
1. A composition of matter comprising:

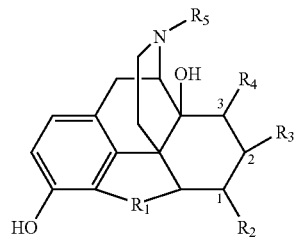

wherein
$R_1$ is O, NH, $NR_6$, S, SH, or $SR_6$;
$R_2$ is H, =O, t-butyl, phenoxy, diphenylamine, thiophenyl, phenyl, or cyclohexane;
$R_3$ is phenoxy;
wherein $R_2$ and $R_3$ comprise a ring system selected from:

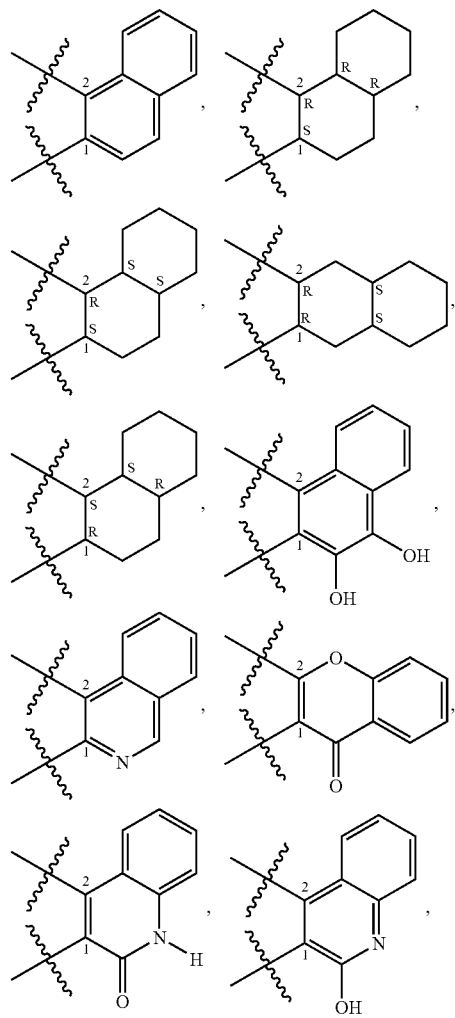

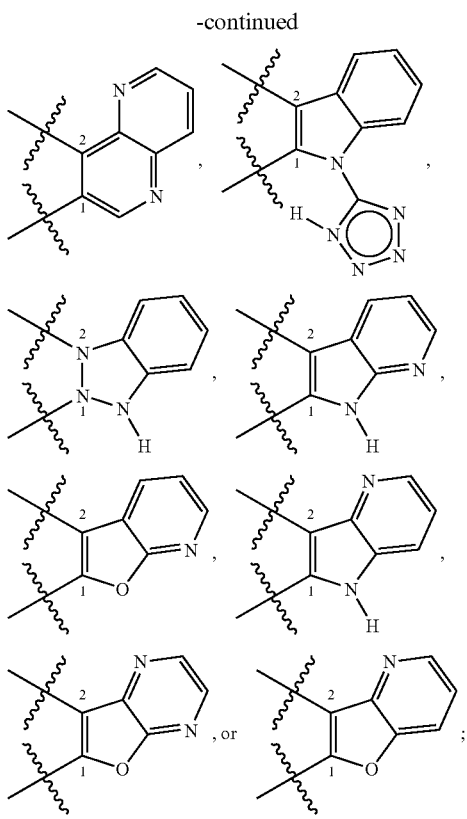

or wherein R₃ and R₄ comprise a ring system selected from:

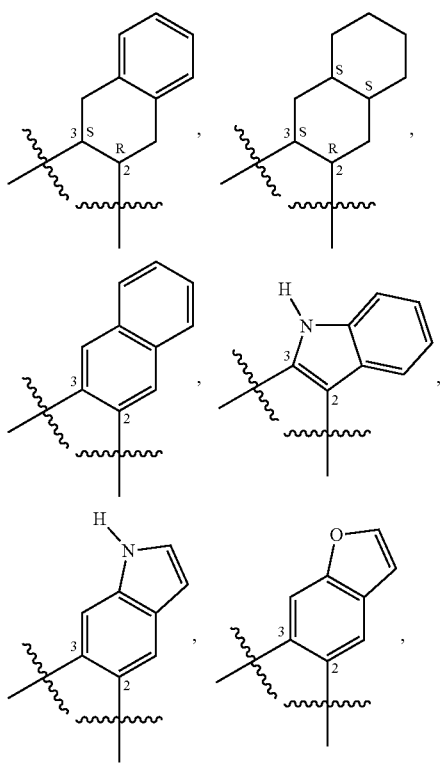

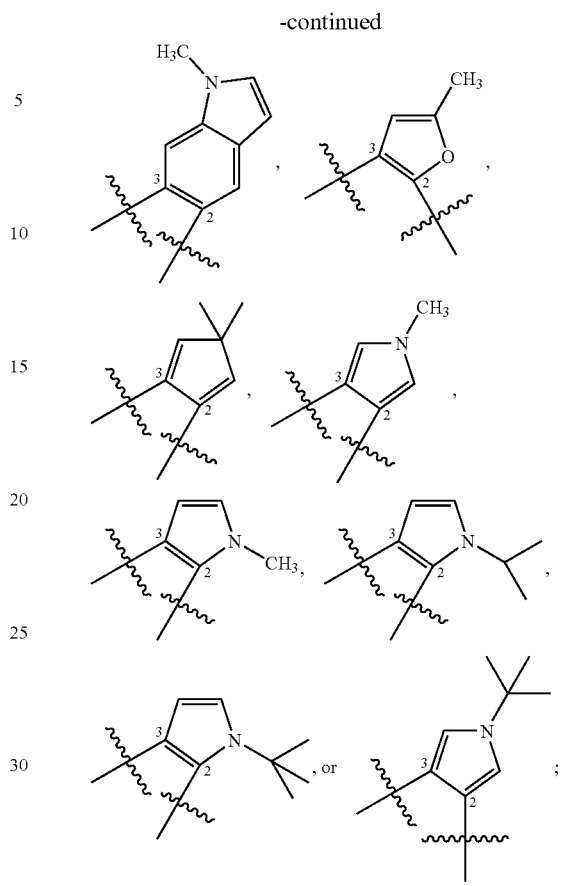

or
R₄ is H or t-butyl; and
R₅ is CH₃, methylcyclopropane, a linear alkyl, a branched alkyl, a substituted alkyl, or a substituted branched alkyl;
R₆ is H, CH₃, a linear alkyl, a branched alkyl, a substituted alkyl, or a substituted branched alkyl; or
a pharmaceutically acceptable salt thereof.

2. The composition of claim 1, wherein
R₁ is O, or NH;
R₂ and R₃ comprise a ring system selected from:

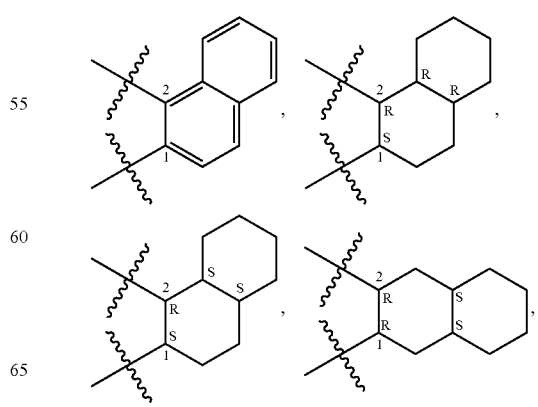

-continued
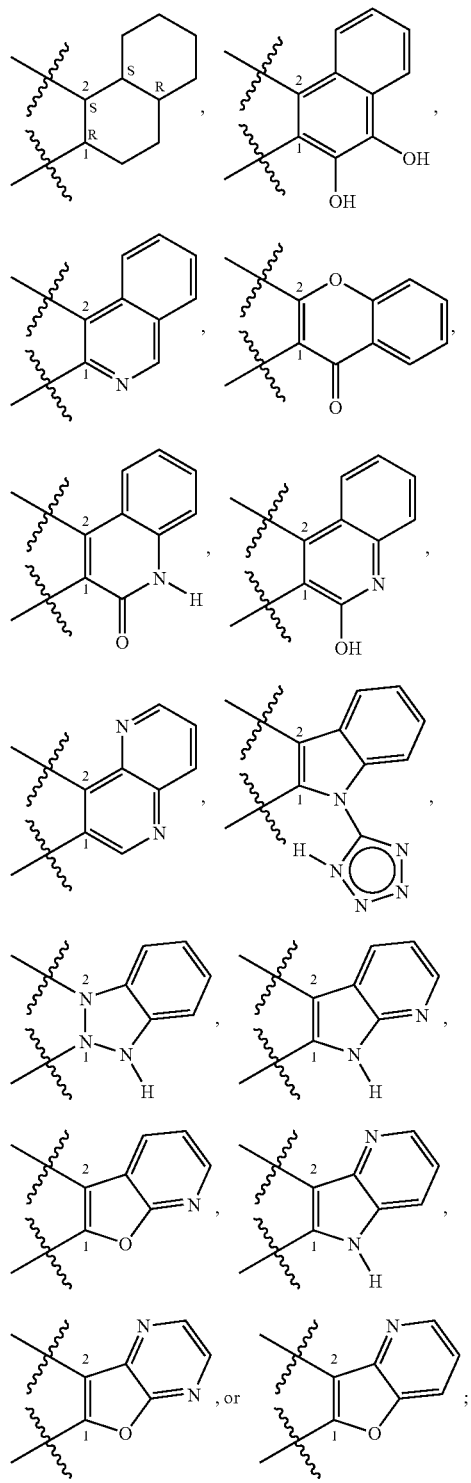
R$_4$ is H;
R$_5$ is methylcyclopropane; or
or a pharmaceutically acceptable salt thereof.
3. The composition of claim 1, wherein
R$_1$ is O, or NH;
R$_2$ is =O;
R$_3$ and R$_4$ comprise a ring system selected from:
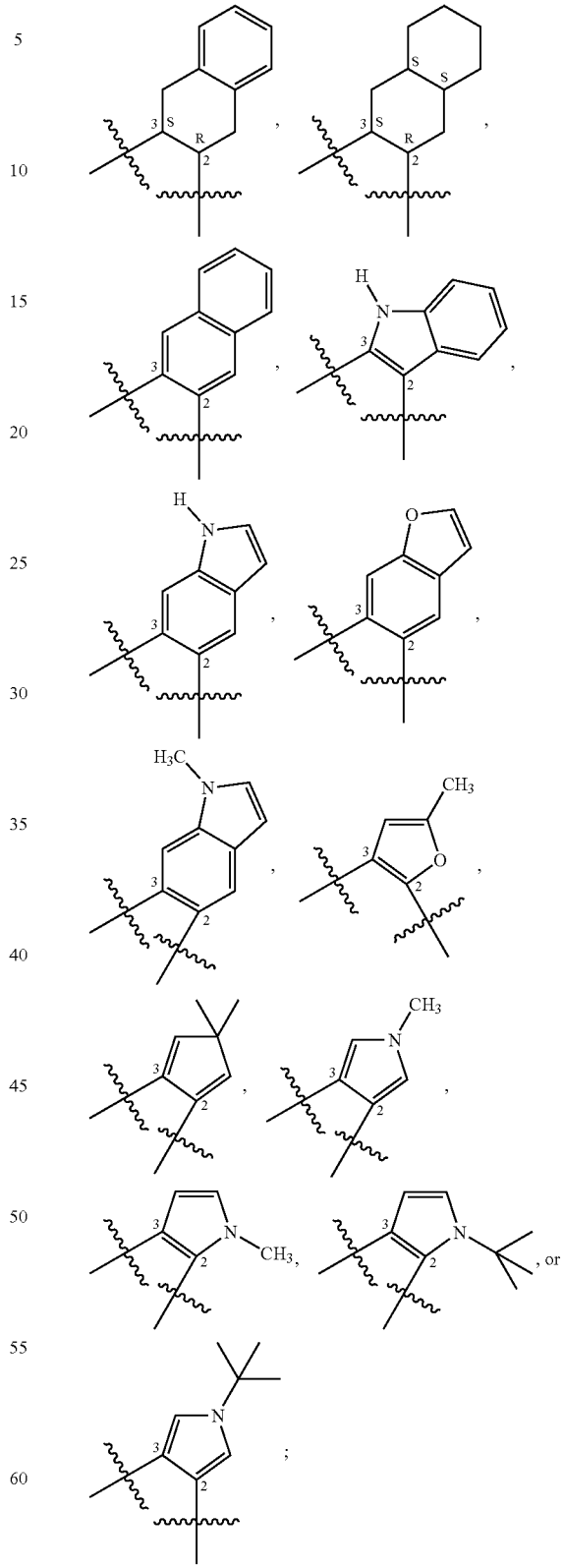
R$_5$ is methyl; or
a pharmaceutically acceptable salt thereof.

4. The composition of claim 1, wherein
$R_1$ is O, or NH;
$R_2$ is H, or =O;
$R_3$ is phenoxy;
$R_4$ is H or t-butyl; and
$R_5$ is $CH_3$, methylcyclopropane, a linear alkyl, a branched alkyl, a substituted alkyl, or a substituted branched alkyl;
or a pharmaceutically acceptable salt thereof.

5. The composition of claim 4, wherein $R_5$ is $CH_3$ or methylcyclopropane.

6. The composition of claim 1, wherein
$R_1$ is O, or NH;
$R_4$ is H;
$R_5$ is methyl; and
$R_2$ and $R_3$ comprise:

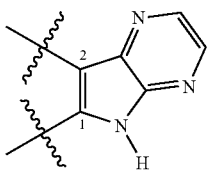

or a pharmaceutically acceptable salt thereof.

7. The composition of claim 1, wherein
$R_1$ is O, or NH;
$R_2$ is =O;
$R_3$ and $R_4$ comprise:

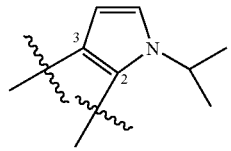

$R_5$ is methylcyclopropyl; or
a pharmaceutically acceptable salt thereof.

8. A pharmaceutical composition comprising a compound according to claim 1 and a pharmaceutically acceptable carrier.

9. A pharmaceutical composition comprising a compound according to claim 7 and a pharmaceutically acceptable carrier.

* * * * *